United States Patent [19]

Brickner

[11] Patent Number: 5,247,090
[45] Date of Patent: Sep. 21, 1993

[54] TRICYCLIC [6,6,5]-FUSED OXAZOLIDINONE ANTIBACTERIAL AGENTS

[75] Inventor: Steven J. Brickner, Portage, Mich.

[73] Assignee: The Upjohn Company, Kalamazoo, Mich.

[21] Appl. No.: 6,596

[22] Filed: Jan. 21, 1993

Related U.S. Application Data

[60] Division of Ser. No. 882,407, May 13, 1992, Pat. No. 5,231,188, which is a continuation-in-part of Ser. No. 553,795, Jul. 13, 1990, abandoned, which is a continuation-in-part of Ser. No. 438,759, Nov. 17, 1989, abandoned.

[51] Int. Cl.⁵ .......................................... C07D 498/04
[52] U.S. Cl. ..................................... 546/89; 546/92; 544/126
[58] Field of Search ................... 544/126; 546/89, 92

[56] References Cited

FOREIGN PATENT DOCUMENTS 0322263  6/1989  European Pat. Off. ............ 546/270

Primary Examiner—Bernard Dentz
Assistant Examiner—Phyllis G. Spivack
Attorney, Agent, or Firm—Bruce Stein

[57] ABSTRACT

The present invention involves tricyclic-fused 6-member ring oxazolidinones

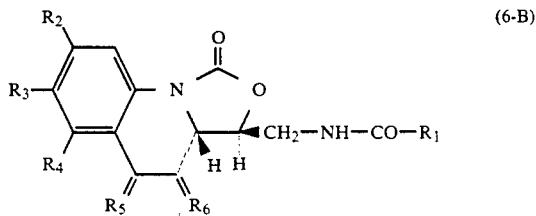

which are useful as antibacterial agents.

8 Claims, No Drawings

TRICYCLIC [6,6,5]-FUSED OXAZOLIDINONE ANTIBACTERIAL AGENTS

CROSS REFERENCE TO RELATED APPLICATIONS

The present patent application is a divisional application of U.S. patent application Ser. No. 07/882,407, filed May 13, 1992 now U.S. Pat. No. 5,231,188 which is the national phase of PCT/US90/06220, filed Nov. 2, 1990, which is a continuation-in-part of Ser. No. 07/553,795, filed Jul. 13, 1990, now abandoned, which is a continuation-in-part of Ser. No. 07/438,759, filed Nov. 17, 1989, now abandoned.

BACKGROUND OF THE INVENTION

1. Field of the Invention

The present invention relates to tricyclic-fused six [6,6,5] member ring oxazolidinones which are useful as antibacterial agents.

2. Description of the Related Art

U.S. Pat. No. 4,128,654 discloses 5-halomethylphenyl-2-oxazolidinones which are useful in controlling fungal and bacterial diseases of plants.

U.S. Pat. No. 4,250,318 discloses 3-substituted phenyl-5-hydroxymethyloxazolidinones having antidepressive utility.

U.S. Pat. No. Re. 29,607 discloses 3-substituted phenyl-5-hydroxymethyloxazolidinones having antidepressive, tranquilizing and sedative utility.

U.S. Pat. No. 4,340,606 discloses 3-(p-alkylsulfonyl)-phenyl-5-(hydroxymethyl or acyloxymethyl)oxazolidinones having antibacterial activity in mammals.

Belgium Pat. No. 892,270 discloses 3-(arylalkyl, arylalkenyl or arylacetylenic substituted)phenyl)-5-(aminomethyl)oxazolidinones which are inhibitors of monoamine oxidase.

U.S. Pat. No. 4,461,773 discloses 3-substituted phenyl-5-hydroxymethyloxazolidinones which have antibacterial activity.

European Pat. Publications Nos. 127,902 and 184,170 disclose 3-substituted phenyl-5-amidomethyloxazolidinones which have antibacterial utility.

Antimicrobial Agents and Chemotherapy 1791 (1987) discusses compunds disclosed in European Patent Publications Nos. 127,902 and 184,170, discussed above, and compares these new compounds with known antibiotics.

U.S. Pat. No. 4,705,799 discloses aminomethyloxooxazolidinyl benzene derivatives including sulfides sulfoxides, sulfones and sulfonamides which posses antibacterial activity.

U.S. Pat. No. 4,801,600 (WANG) discloses 6'-indolinyl- or alkanoneoxazolidinones (where the indolinyl nitrogen is meta to the oxazolidinone nitrogen). WANG also discloses oximinooxazolidinones.

The tricyliy-fused 5 [6,5,5] and 6 [6,6,5] member ring oxazolidinones (5) and (6) of the present invention differ from those of WANG.

PCT/US89/03548 application discloses 5'indolinyl-5$\beta$-amidomethyloxazolidinones, 3-(fused-ring substituted)phenyl-5$\beta$-amidomethyloxazolidinones, and 3-(nitrogen substituted)phenyl-5$\beta$-amidomethyloxazolidinones which are useful as antibacterial agents. None of those compounds are oxazolidinones fused at $C_4$ and nitrogen with other rings.

Other recent references disclosing various oxazolidinones include U.S. Pat. Nos. 4,801,600, 4,921,869, EP 312,000, J. Med. Chem. 32, 1673 (1989) and Tetrahedron 45, 1323 (1989).

European Patent Publication 352,781 discloses phenyl and pyridinyl substituted phenyl oxazolidinones.

European Patent Publication 316,594 discloses 3-substituted styryl oxazolidinones.

European Patent Publication 312,000 discloses phenylmethyl and pyridinylmethyl substituted phenyl oxazolidinones.

SUMMARY OF INVENTION

Disclosed is a cis tricyclic-fused 6-member ring oxazolidinones of formula (6-A) where (I) $R_1$ is —H, $C_1$-$C_{12}$ alkyl optionally substituted with 1-3 Cl, $C_3$-$C_{12}$ cycloalkyl, $C_5$-$C_{12}$ alkenyl containing one double bond, —$\phi$ optionally substituted with 1-3 —OH, —OCH$_3$, —OC$_2$H$_5$, —NO$_2$, —F, —Cl, —Br, —COOH and —SO$_3$H, —N($R_{1-1}$)($R_{1-2}$) where $R_{1-1}$ and $R_{1-2}$ are the same or different and are —H, $C_1$-$C_2$ alkyl, furanyl, tetrahydrofuranyl, 2-thiophene, pyrrolidinyl, pyridinyl, —O—$R_{1-3}$ where $R_{1-3}$ is $C_1$-$C_4$ alkyl,

—NH$_2$,

—NHR$_{1-4}$ where $R_{1-4}$ is $C_1$-$C_3$ alkyl or —$\phi$,

—NR$_{1-4}$R$_{1-5}$ where $R_{1-5}$ is $C_1$-$C_3$ alkyl and $R_{1-4}$ is as defined above, and where $R_{1-4}$ and $R_{1-5}$ can be taken together with the attached nitrogen atom to form a saturated mononitrogen $C_5$-$C_7$ heterocyclic ring including —O— (morpholine),

—CH$_2$—OH,

—CH$_2$—OR$_{1-6}$ where $R_{1-6}$ is $C_1$-$C_4$ alkyl or —CO—$R_{1-7}$ where $R_{1-7}$ is $C_1$-$C_4$ alkyl or —$\phi$;

(II) $R_2$ and $R_4$ are the same or different and are

—H,

—OH,

—F, —Cl, —Br, I,

—O—CO—$R_{2-1}$ where $R_{2-1}$ is $C_1$-$C_3$ alkyl or —$\phi$, (III) $R_3$ is —H, —F, —Cl, —Br, —I, —O—CH$_3$, —O—C$_2$H$_5$, —CO—$R_{3-1}$ where $R_{3-1}$ is $C_1$-$C_4$ alkyl optionally substituted with 1 or 2 —F or —Cl, or 1 —OH, —CO—CH$_2$—O—CH$_2$—$\phi$, —CO—CH$_2$—O—$R_{3-2}$ where $R_{3-2}$ is $C_1$-$C_2$ alkyl or —$\phi$,

—CO—CH$_2$—N$_3$,

—CO—CH$_2$—NH—CO—$R_{3-3}$ where $R_{3-3}$ is $C_1$-$C_2$ alkyl or —$\phi$,

—C(CH$_3$)=N—OH,

—C(CH$_3$)=N—O—$R_{3-4}$ where $R_{3-4}$ is $C_1$-$C_2$ alkyl

—CO—CH$_2$—NR$_{3-5}$R$_{3-6}$ where $R_{3-5}$ is —H, —CH$_3$, —C$_2$H$_5$ or —$\phi$ and where $R_{3-6}$ is —H, —CH$_3$ or —C$_2$H$_5$,

—SO$_2$—CH$_3$,

—SO$_2$—$\phi$,

—SO—CH$_3$,

—SO—$\phi$,

—SO$_2$—NH$_2$,

—S—$R_{3-7}$ where $R_{3-7}$ is —H, —CH$_3$, —C$_2$H$_5$ or —$\phi$,

—CO—CH$_2$—O—CO—$R_{3-8}$ where $R_{3-8}$ is $C_1$-$C_6$ alkyl or —$\phi$,

—$\phi$ optionally substituted by —CN,

—C≡CH, —C≡C—CH$_3$, —C≡C—CH$_2$—OH,

—N$_3$, —NO$_2$,

—O—[$C_1$-$C_4$ alkyl],
—COOH, —$SO_2$—OH,
—F, —Cl, —Br, —I, —OH,
—$NH_2$, —N($R_{3-9}$)($R_{3-10}$) where $R_{3-9}$ and $R_{3-10}$ are the same or different and are selected from the group consisting of —H, $C_1$-$C_3$ alkyl or —$\phi$,
1-pyrrolidyl,
—CO—[$C_1$-$C_4$ alkyl], —CO—$CH_2$—OH, —CO—$CH_2$—$N_3$,
—CHOH—[$C_1$-$C_4$ alkyl], —$CH_2$—OH,
—$CH_2$—$NH_2$, —$CH_2$—N($R_{3-9}$)($R_{3-10}$) where $R_{3-9}$ and $R_{3-10}$ are as defined above,
—$CH_2$—$N_3$,
—$CH_2$—NH—CO—$R_{3-9}$ where $R_{3-9}$ is as defined above,
—S—[$C_1$-$C_4$ alkyl], —SO—[$C_1$-$C_4$ alkyl], —$SO_2$—[$C_1$-$C_4$ alkyl],
—($CH_3$)=N—OH, —($CH_3$)=N—O—[$C_1$-$C_4$ alkyl],
—NH—COO—[$C_1$-$C_4$ alkyl], —NH—$SO_2$—[$C_1$-$C_4$ alkyl],
—NH—CO—[$C_1$-$C_4$ alkyl], —NH—CO—$\phi$,
—S—CN,
—$\phi$ optionally substituted with 1 or 2 —F, —Cl, —OH,
—CO—N($R_{3-9}$)($R_{3-10}$) where $R_{3-9}$ and $R_{3-10}$ are as defined above,
$C_1$-$C_{12}$ alkyl, $C_2$-$C_{12}$ alkenyl containing 1, 2 or 3 double bonds,
—C*H=CH—CH=Z—Y=W*— where the atoms or symbols representing an atom marked with an asterisk (*) are bonded to each other resulting in the formation of a ring where one of Z, Y and W is —N= and the others are —CH=, optionally substituted with —H, C1-C4 alkyl, —NO2, —$NH_2$, —NH—CO—[$C_1$-$C_4$ alkyl], —CN, —COOH, —O—[$C_1$-$C_4$ alkyl], —F, —Cl, —Br, I and the N—oxides thereof,
with the proviso that at least one of $R_2$, $R_3$ and $R_4$ is —H,
(IVA) $R_5$ is $R_{5-1}$:$R_{5-2}$ and $R_6$ is $R_{6-1}$:$R_{6-2}$ where one of $R_{5-1}$ or $R_{5-2}$ is taken with one of $R_{6-1}$ or $R_{6-2}$ to form a second bond between the carbon atoms to which they are attached and the other of $R_{5-1}$ or $R_{5-2}$ and $R_{6-1}$ or $R_{6-2}$ is —H,
(IVB) $R_5$ is $R_{5-3}$:$R_{5-4}$ where one of $R_{5-3}$ and $R_{5-4}$ is —H and the other of $R_{5-3}$ and $R_{5-4}$ is —H, —OH or —O—CO—$R_{5-5}$ where $R_{5-5}$ is $C_1$-$C_3$ alkyl or —$\phi$ optionally substituted with 1 or 2 —F, —Cl, —OH, or —$OCH_3$,
(IVC) $R_6$ is $R_{6-3}$:$R_{6-4}$ where one of $R_{6-3}$ and $R_{6-4}$ is —H and the other of $R_{6-3}$ and $R_{6-4}$ is —H, —OH or —O—CO—$R_{6-5}$ where $R_{6-5}$ is $C_1$-$C_3$ alkyl or —$\phi$ optionally substituted with 1 or 2 —F, —Cl, —OH, or —$OCH_3$, and pharmaceutically acceptable salts thereof.
Also disclosed is a tricyclic-fused 5-member [6,5,5] ring oxazolidinone of formula (5) where
(I) $R_1$ is —H,
$C_1$-$C_{12}$ alkyl optionally substituted with 1-3 Cl,
$C_3$-$C_{12}$ cycloalkyl,
$C_5$-$C_{12}$ alkenyl containing one double bond,
—$\phi$ optionally substituted with 1-3 —OH, —$OCH_3$, —$OC_2H_5$, —$NO_2$, —F, —Cl, —Br, —COOH and —$SO_3H$, —N($R_{1-1}$)($R_{1-2}$) where $R_{1-1}$ and $R_{1-2}$ are the same or different and are —H, $C_1$-$C_2$ alkyl,
furanyl,
tetrahydrofuranyl,
2-thiophene,
pyrrolidinyl,
pyridinyl,
—O—$R_{1-3}$ where $R_{1-3}$ is $C_1$-$C_4$ alkyl,
—$NH_2$,
—$NHR_{1-4}$ where $R_{1-4}$ is $C_1$-$C_3$ alkyl or —$\phi$, —$NR_{1-4}R_{1-5}$ where $R_{1-5}$ is $C_1$-$C_3$ alkyl and $R_{1-4}$ is as defined above, and where $R_{1-4}$ and $R_{1-5}$ can be taken together with the attached nitrogen atom to form a saturated mononitrogen $C_5$-$C_7$ heterocyclic ring including —O— (morpholine),
—$CH_2$—OH,
—$CH_2$—$OR_{1-6}$ where $R_{1-6}$ is $C_1$-$C_4$ alkyl or —CO—$R_{1-7}$ where $R_{1-7}$ is $C_1$-$C_4$ alkyl or —$\phi$;
(II) $R_2$ and $R_4$ are the same or different and are —H,
—OH,
—F, —Cl, —Br, —I,
—O—CO—$R_{2-1}$ where $R_{2-1}$ is $C_1$-$C_3$ alkyl or —$\phi$,
(III) $R_3$ is —H, —F, —Cl, —Br, —I, —O—$CH_3$, —O—$C_2H_5$,
—CO—$R_{3-1}$ where $R_{3-1}$ is $C_1$-$C_4$ alkyl optionally substituted with 1 or 2 —F or —Cl, or 1 —OH,
—CO—$CH_2$—O—$CH_2$—$\phi$,
—CO—$CH_2$—O—$R_{3-2}$ where $R_{3-2}$ is $C_1$-$C_2$ alkyl or —$\phi$,
—CO—$CH_2$—$N_3$,
—CO—$CH_2$—NH—CO—$R_{3-3}$ where $R_{3-3}$ is $C_1$-$C_2$ alkyl or —$\phi$,
—C($CH_3$)=N—OH,
—C($CH_3$)=N—O—$R_{3-4}$ where $R_{3-4}$ is $C_1$-$C_2$ alkyl
—CO—$CH_2$—$NR_{3-5}R_{3-6}$ where $R_{3-5}$ is —H, —$CH_3$, —$C_2H_5$ or —$\phi$ and where $R_{3-6}$ is —H, —$CH_3$ or —$C_2H_5$,
—$SO_2$—$CH_3$,
—$SO_2$—$\phi$,
—SO—$CH_3$,
—SO—$\phi$,
—$SO_2$—$NH_2$,
—S—$R_{3-7}$ where $R_{3-7}$ is —H, —$CH_3$, —$C_2H_5$ or —$\phi$,
—CO—$CH_2$—O—CO—$R_{3-8}$ where $R_{3-8}$ is $C_1$-$C_6$ alkyl or —$\phi$,
—$\phi$ optionally substituted by —CN,
—C≡CH, —C≡C—$CH_3$, —C≡C—$CH_2$—OH,
—$N_3$, —$NO_2$,
—O—[$C_1$-$C_4$ alkyl],
—COOH, —$SO_2$—OH,
—F, —Cl, —Br, —I, —OH,
—$NH_2$, —N($R_{3-9}$)($R_{3-10}$) where $R_{3-9}$ and $R_{3-10}$ are the same or different and are selected from the group consisting of —H, $C_1$-$C_3$ alkyl or —$\phi$,
1-pyrrolidyl,
—CO—[$C_1$-$C_4$ alkyl], —CO—$CH_2$—OH, —CO—$CH_2$—$N_3$,
—CHOH—[$C_1$-$C_4$ alkyl], —$CH_2$—OH,
—$CH_2$—$NH_2$, —$CH_2$—N($R_{3-9}$)($R_{3-10}$) where $R_{3-9}$ and $R_{3-10}$ are as defined above,
—$CH_2$—$N_3$,
—$CH_2$—NH—CO—$R_{3-9}$ where $R_{3-9}$ is as defined above,
—S—[$C_1$-$C_4$ alkyl], —SO—[$C_1$-$C_4$ alkyl], —$SO_2$—[$C_1$-$C_4$ alkyl],
—($CH_3$)=N—OH, —($CH_3$)=N—O—[$C_1$-$C_4$ alkyl],
—NH—COO—[$C_1$-$C_4$ alkyl], —NH—$SO_2$—[$C_1$-$C_4$ alkyl],
—NH—CO—[$C_1$-$C_4$ alkyl], —NH—CO—$\phi$,
—S—CN, —φ optionally substituted with 1 or 2 —F, —Cl, —OH, —CO—N($R_{3-9}$)($R_{3-10}$) where $R_{3-9}$ and $R_{3-10}$ are as defined above, $C_1$-$C_{12}$ alkyl, $C_2$-$C_{12}$ alkenyl containing, 1, 2 or 3 double bonds, —C*H=CH—CH=Z—Y=W*— where the atoms or symbols representing an atom marked with an asterisk (*) are bonded to each other resulting in the formation of a ring where one of Z, Y and W is —N= and the others are —CH=, optionally substituted with —H, C1-C4 alkyl, —NO2, —NH2, —NH—CO—[$C_1$-$C_4$ alkyl], —CN, —COOH, —O—[$C_1$-$C_4$ alkyl], —F, —Cl, —Br, I and the N-oxides thereof, with the proviso that at least one of $R_2$, $R_3$ and $R_4$ is —H, (IVA) $R_7$ is $R_{7-1}$:$R_{7-2}$ where one of $R_{7-1}$ and $R_{7-2}$ is taken with $R_8$ to form a second bond between the carbon atoms to which they are attached and the other of $R_{7-1}$ and $R_{7-2}$ is —H, $C_1$-$C_3$ alkyl, —Cl, —Br, —I, (IVB) $R_8$ is —H and $R_7$ is $R_{7-3}$:$R_{7-4}$ where $R_{7-3}$ and $R_{7-4}$ are each —H or —CH$_3$, (IVC) $R_8$ is —H and $R_7$ is —CO—, (IVD) $R_8$ is —H and $R_7$ is $R_{7-5}$:$R_{7-6}$ where one of $R_{7-5}$ and $R_{7-6}$ is —OH and the other of $R_{7-5}$ and $R_{7-6}$ is —H or —CH$_3$, and pharmaceutically acceptable salts thereof.

Further disclosed is a trans tricyclic-fused 6-member [6,6,5] ring oxazolidinones of formula (6-B) where (I) $R_1$, $R_2$, $R_3$, $R_4$, $R_5$ and $R_6$ are as defined above for the cis tricyclic-fused 6-member oxazolidinones and pharmaceutically acceptable salts thereof.

DETAILED DESCRIPTION OF THE INVENTION

The pharmaceutically active tricyclic-fused 5 member ring [6,5,5] oxazolidinones (5) and tricyclic-fused 6-member ring [6,6,5] oxazolidinones (6) of this invention are prepared by methods well known to those skilled in the art from known starting materials by a variety of methods. Following CHARTS A-E without more, one skilled in the art could readily prepare the tricyclic-fused 5 member [6,5,5] ring oxazolidinones (5) and tricyclic-fused 6-member [6,6,5] ring oxazolidinones (6) of this invention.

CHART A demonstrates a method of preparation of the saturated tricyclic-fused 5 member [6,5,5] ring oxazolidinones [(5), exemplified by (X) and (XI)]. One starts with the indole esters (I), which are well known to those skilled in the art or can readily be prepared from known compounds by methods known to those skilled in the art. $X_1$ is a simple alkyl group such as methyl or ethyl, preferably methyl. The indole ester (I) is reduced to the corresponding indoline ester (II) by reaction with magnesium in methanol. The indoline ester (II) is converted to the corresponding protected indoline ester (III) by reaction with a reagent such as benzyl chloroformate ($X_2$ is —CH$_2$—φ) producing the carbobenzyloxy protected indoline ester (III). Other operable $X_2$ groups include t-butyl and —CH$_2$—φ—O—CH$_3$. Next, the protected indoline ester (III) is reduced producing the hydroxymethyl compound (IV) utilizing reducing agents such as lithium or sodium borohydride or alternatively with diisobutylaluminumhydride to give directly the aldehyde (V); preferred is lithium borohydride in tetrahydrofuran. The hydroxymethyl compound (IV) is then oxidized to the corresponding aldehyde (V) by Swern oxidation (oxalyl chloride, dimethylsulfoxide and triethylamine) or pyridinium chlorochromate; preferred is the Swern oxidation method. The aldehyde (V) is then converted to the corresponding cyanohydrin (VI) by reaction with acetone cyanohydrin in the presence of a weak base such as potassium carbonate. When the cyanohydrin (VI) is formed, two diastereomers of the cyanohydrin produced. They are designated A (less polar by TLC) and B (more polar by TLC). Diastereomer B ultimately is transformed into tricyclic-fused 5 member [6,5,5] ring oxazolidinones (5) having trans configuration at positions 1 and 9a of the oxazolidinone (positional numbering system here refers to that of the oxazolidinone ring only see CHART F) with the amidomethyl side chain in the "β" configuration. The cyanohydrin (VI), either each diastereomer individually or as a mixture, is then reduced to the amino compound (VII) by reaction with a reducing agent. Suitable reducing agents include, for example, borane-dimethylsulfide, or when $X_2$ is t-butyl, Raney nickel in acetic anhydride and sodium acetate; preferred is borane-dimethylsulfide.

All the compounds beginning with the indoline esters (II) up thru the amino compounds (VII) have an asymmetric center at what will become the $C_1$-position (IUPAC nomenclature) of the oxazolidinone ring. Because of this asymmetric center there are two enantiomers, providing a racemic mixture. The enantiomer which is pharmacologically active is the enantiomer with the "S" configuration, having the 1β-amidomethyl substituent, see CHART F. With the tricyclic-fused 5 member ring oxazolidinones, only the trans diastereomer is biologically active. The racemic mixture is useful in the same way and for the same purpose as the pure S-enantiomer; the difference is that twice as much racemic material must be used to produce the same effect as the pure S-enantiomer. If desired, the mixture of enantiomers is resolved by means known to those skilled in the art. It is preferable to resolve the racemic mixture at the stage of the amino compounds (VII) using methods known to those skilled in the art, see for example, Optical Resolution Procedures for Chemical Compounds, Vol 1,: Amines and Related Compounds, Paul Newman, Optical Resolution Information Center, Manhattan College, Riverdale, N.Y., 10471, 1978. For example, treatment of the d,1-amino mixture (VII) with an optically active acid such as (+)-tartaric acid or alternatively with (−)-tartaric acid, would yield a mixture of diastereomeric salts, which can be separated most conviently by fractional crystallization to give a salt containing only one enantiomer of the racemic mixture. Other suitable optically active acids include, (−) dibenzoyltartaric acid, (+)-camphoric acid, (+)- and (−)-malic acid and (+)-camphor-10-sulfonic acid. By reacting the diastereomeric salt with a base one obtains the enantiomer as the free amino compound (VII). These optically pure compounds are then used in the same way as the racemic mixture.

The amino compound (VII), either racemic or optically pure, is then selectively monoacylated with an acylating agent selected from the group of compounds of the formula ($R_1$—CO)$_2$—O or $R_1$—CO—Cl in the usual manner to produce the amide (VIII). The amide (VIII) is then N-deprotected (—CO$_2$—$X_2$ group is removed) by hydrogenation using a reagent such as palladium on carbon (10%) or when $X_2$ is t-butyl, acidic treatment, to produce the unprotected indoline (IX). The unprotected indoline (IX) is then cyclized to form the tricyclic fused oxazolidinone (X) by one of three methods. First, treatment with phosgene results in cyclizing the unprotected indoline (IX) to form the tricyclic-fused 5 member [6,5,5] ring oxazolidinones (5). Secondly, when acylating the amino compound (VII) to produce the amide (VIII) the bisacylated compound (XII) may be produced depending on a number of circumstances, including the amount of acylating agent present, the length of time of reaction, the temperature, etc. The bisacylated compound (XII) can also be converted to the tricyclic compound (X) by mild saponification. This route (VII→XII→X) is a step shorter than the previously described route (VII→VIII→IX→X). Thirdly, the amide (VIII) can be converted to the tricyclic compound (X) by mild treatment with base such as sodium or potassium hydroxide. In the case of diastereomer A (RS,SR), treatment with phosgene first gives the isolatable intermediate N-carbonyl chloride-alcohol, which is subsequently closed to the oxazolidinone with a base such as triethylamine, ethyl diisopropylamine or dilute sodium or potassium hydroxide or ethoxide. In many cases the tricyclic fused oxazolidinone (X) will be the desired tricyclic-fused 5 member [6,5,5] ring oxazolidinone (5) because the substitution of $X_3$ will be within the scope of the desired substitutent $R_3$. $X_3$ includes —H, —F, —Cl, —OCH$_3$ and —O—C$_2$H$_5$; preferred is —H. This will not always be the case because a number of substituents within the scope of $R_3$ will not survive the synthetic reaction sequence beginning with (I) and ending with (X). In those cases, the desired $R_3$ substitutent is added to the tricyclic fused oxazolidinone (X) to form the desired tricyclic-fused 5 member [6,5,5] ring oxazolidinones (5). Reactions of this type include Friedel-Crafts acylation where $X_3$ is —H, see, for example, J. Gen. Chem. USSR 29,2541 (1959) and Russ. Chem. Rev. 36, 753 (1967). Reagents useful for the Friedel-Crafts acylation include carboxylic acids or acid chlorides or anhydrides, such as (CH$_3$CO)$_2$O and Cl —CH$_2$—CO—Cl. In the latter case, following the Friedel-Crafts addition, replacing $X_3$ with —CO—CH$_2$—Cl, the terminal —Cl is reacted further to produce the desired $R_3$. The terminal —Cl is replaced by a variety of functional groups (group), as is known in the art, for example, by reduction with hydrogen on palladium or zinc and acetic acid (—H), hydrolysis with dilute base (hydroxide, alkoxide), amine displacement (—NH$_2$, —NH$_3$+, —NR$_{3-5}$R$_{3-6}$), alcohol displacement (—OR$_{3-2}$), azide displacement (N$_3$), mercaptan displacement (—SR$_{3-7}$), or carboxylate (—O—CO—R$_{3-8}$). The amines can readily be acylated to form —CO—CH$_2$—N—CO—substituent. Reactions of this type also include bromination or iodination to give the intermediate arylbromide or aryliodide. This can then be replaced with an aryl or heteroaryl group using aryltrimethyltin or pyridyltrimethyltin or instead, aryl boronic acid reagents in the presence of a catalytic amount of palladium (0) catalyst, such as tetrakis(triphenylphosphine)palladium (0).

By starting with a appropriate indole-2-carboxylic acid ester (XII) either commercially available or readily prepared by any of numerous methods known to those skilled in the art, the monomethyl substituted compound (one of $R_{7-1}$ or $R_{7-2}$ is —CH$_3$ and the other is —H) is readily prepared.

Following the general procedure of CHART A and making non-critical variations but starting with the appropriate corresponding non-aromatic 6 member ring (instead of 5 member), that is starting with the appropriate dihydro- or tetrahydroquinoline, the tricyclic-fused 6 member [6,6,5] ring oxazolidinones (6) compounds are obtained. The tricyclic-fused 6 member [6,6,5] ring oxazolidinones (6) compounds in which one or both of $R_5$ and/or $R_6$ contain a hydroxyl group are prepared from the dihydroquinoline derived analog, $R_5$ and $R_6$ are each —H (—CH=CH—) by reaction with osmium tetroxide for the diol ($R_5$ and $R_6$ are each —H:—OH) and by a hydroboration reaction for the monohydroxy compound (one of $R_5$ and $R_6$ is —H:—H and the other is —H:—OH).

CHART B discloses the preparation of both tricyclic-fused 5 member [6,5,5] ring oxazolidinones (5) and tricyclic-fused 6 member [6,6,5] ring oxazolidionones (6), where the carbon-carbon bond $\alpha$ to the nitrogen is formed by a known method, see J. Am. Chem. Soc., 106, 3270 (1984). This is a very versatile method and permits use of a wide variety of substitutents for $Q_1$. $Q_1$ ultimately includes the following substitution, —CH$_2$—CH$_2$—, —CH=CH—, —CHOH—CH$_2$—, —CH$_2$—CHOH—, —CHOH—CHOH—, —CH=, —C(-C$_1$-C$_3$ alkyl)=, —CH$_2$, —CHCH$_3$—, —CO—, —C(CH$_3$)$_2$— and —CCH$_3$OH— though some of these can not be present in the starting material and must be derived from other —Q$_1$— substituents as explained below. It is preferred that Q$_1$ be —CH$_2$— or —CH$_2$—CH$_2$—. The aromatic amine (XIII) is activated for formation of an anion $\alpha$ to the nitrogen by the attachment of the t-butyl formamidine to give the t-butyl formamidine (XIV). Next, the t-butyl formamidine (XIV) is deprotonated with an appropriate base and then reacted with an N-protected glycinal to form the protected hydroxyamine (XV), which is followed by removal of the formamidine and then ring closure with phosgene to form the protected oxazolidinone (XVI) from which the protecting group is removed to form the amino oxazolidinone (XVII). The amino oxazolidinone (XVII) is then acylated to form the tricyclic-fused 5/6-member oxazolidinone (XVIII). As with the tricyclic-fused oxazolidinone (X) $X_3$ may have to be converted to $R_3$ to obtain the desired substituent.

CHART C discloses that the tricyclic-fused 5 member ring oxazolidinones can readily be converted to other tricyclic-fused 5 member ring oxazolidinones. More specifically, for the tricyclic-fused 5/6 oxazolidinones (XVIII) where $Q_1$ is —CO—, the carbonyl group is reacted with the appropriate Grignard reagent $R_{7-1}$—Mg—X to produce the alkyl-hydroxy compound (XX). This alkyl-hydroxy compound (XX), if desired, can be dehydrated with acid to produce the substituted unsaturated compound (XXI). The tricyclic-fused 5/6 member ring oxazolidinones (XVIII) where Q$_1$ is —CO— can also be reacted with hydride producing the corresponding hydroxy compound (XXII) which can be dehydrated, if desired, to the corresponding unsaturated 5-member compound (XXIII) where R—$_{7-2}$ is —H. The unsaturated 5-member compound (XXIII, $R_{7-2}$ is —H) can also be prepared from the corresponding tricyclic-fused 5/6 oxazolidinone (XVIII) where Q$_1$ is —CH$_2$— by reaction with an oxidizing agent such as DDQ. Alternatively, a way of producing the unsaturated 5-member compound (XXIII) where $R_{7-2}$ is —Cl, —Br or —I is by contacting of the tricyclic-fused 5 member ring oxazolidinones (XVIII) with excess N-chlorosuccinimide, N-bromosuccinimide or N-iodosuccinimide in a solvent such as acetonitrile in the presence of benzoylperoxide. When $X_3$ is —H, this position will also be halogenated, and if desired one or both halogens can be reductively removed by treatment with zinc metal in acetic acid to give the corresponding unsaturated 5-member compound (XXIII) where $R_{7-2}$ is —H.

CHART D discloses how the aromatic amine (XIII) starting materials of CHART B are prepared where $Q_1$ is —CHCH$_3$— and —C(CH$_3$)$_2$—. The cyclic amide (XXIV) is contacted with a strong base such as LDA and methyl iodide. Depending on the number of equivalents of LDA and methyl iodide used either one (2 eq LDA +1 eq methyl iodide) or two (3 eq LDA +2 eq methyl iodide) methyl groups are introduced to produce the α-substituted cyclic amide (XXV). The α-substituted cyclic amide (XXV) is then reduced with an agent such as lithium aluminum hydride to produce the desired aromatic amine (XIII).

The tricyclic-fused 5 member [6,5,5] ring oxazolidinones (5) include the tricyclic-fused oxazolidinones (X), the tricyclic-fused 5 member ring oxazolidinones (XI), the tricyclic-fused 5/6 oxazolidinones (XVIII), the tricyclic-fused 5/6-member ring oxazolidinones (XIX), the alkylhydroxy compounds (XX), the substituted unsaturated compounds (XXI), the hydroxy compounds (XXII) and the unsaturated 5-member compounds (XXIII). The tricyclic-fused 6 member ring oxazolidinones (6) include the the tricyclic-fused 5/6 oxazolidinones (XVIII) and the tricyclic-fused 5/6-member ring oxazolidinones (XIX).

CHART E discloses the stereochemistry of the oxazolidinones (XXVI), more particularly the tricyclic-fused 5 member [6,5,5] ring oxazolidinones (5) and tricyclic-fused 6 member [6,6,5] ring oxazolidinones (6). For the tricyclic-fused 5 member [6,5,5] ring oxazolidinones (5), the compounds which are biologically active are the compounds with the stereochemistry as set forth in CHART E. That is the —H at positions 1 and 9a are in the trans configuration, with the absolute configuration at position 1 being "S", see CHART F. The biologically active enantiomer has at the 1-position the amidomethyl side chain in the "β-configuration".

It is preferred that $R_1$ is —H, $C_1$-$C_6$ alkyl, $C_3$-$C_6$ cycloalkyl, —OCH$_3$ and —CHCl$_2$; it is more preferred that $R_1$ is —CH$_3$.

It is preferred that $R_2$ and $R_4$ are both —H.

It is preferred that $R_3$ is —H, —CO—CH$_3$, —CO—CH$_2$—Cl, —CO—CH$_2$—OH, —CO—CHF$_2$, —CO—CH$_2$—N$_3$, —φ, —φ—CN (p), 4-pyridyl, 3-pyridyl and 2-pyridyl; more preferred is —CO—CH$_3$, —φ—CN (p) and 4-pyridyl.

It is preferred that $R_5$ and $R_6$ are both —H.

It is preferred that $R_7$ is —H:—H or —CH$_3$:—CH$_3$.

It is preferred that $R_8$ is —H.

The tricyclic-fused 5 member [6,5,5] ring oxazolidinones (5) and the tricyclic-fused 6 member [6,5,5] ring oxazolidinones (6) of the present invention are useful as antibacterial agents in treating infections in mammals caused by gram-positive and anaerobic infections. It is preferred to treat humans and useful warm-blooded mammals such as cattle, horses, sheep, hogs, dogs, cats, etc.

The tricyclic-fused 5 member [6,5,5] ring oxazolidinones (5) and the tricyclic-fused 6 member [6,6,5] ring oxazolidinones (6) of the present invention are also useful in treating AIDS patients infected with *Mycobacterium avium*.

The tricyclic-fused 5 member [6,5,5] ring oxazolidinones (5) and the tricyclic-fused 6 member [6,6,5] ring oxazolidinones (6) can be administered either parenterally (IV, IM, SQ) or orally. The daily dose is about 5 to about 20 mg/kg. This dose can preferably be given in divided doses and administered 2-4 times daily. The preferred route of administration as well as the particular dosage form for either the parenteral or oral route depends on the particular facts of the situation including the nature of the infection and condition of the patient. The usual pharmaceutical dosage forms appropriate for parenteral (solution, suspension in oil) and oral (tablet, capsule, syrup, suspension, etc) administration are known to those skilled in the art and there is nothing unusual about using those dosage forms with the tricyclic-fused 5 member [6,5,5] ring oxazolidinones (5) and the tricyclic-fused 6 member [6,6,5] ring oxazolidinones (6). The exact dosage of the tricyclic-fused 5 member [6,6,5] ring oxazolidinones (5) and the tricyclic-fused 6 member [6,6,5] ring oxazolidinones (6) to be administered, the frequency of administration, route of administration and the dosage form will vary depending on a number of factors known to those skilled in the art including the age, weight, sex, general physical condition of the patient, the nature of the infection (particular microorganism involved, its virulence, the extent of the infection) other medical problems of the patient, etc as is well known to the physcan treating infectious diseases.

The tricyclic-fused 5 member [6,5,5] ring oxazolidinones (5) and the tricyclic-fused 6 member [6,6,5] ring oxazolidinones (6) can be used either alone or in conjunction with other antibacterial agents as is known to those skilled in the art. Further, the tricyclic-fused 5 member [6,5,5] ring oxazolidinones (5) and the tricyclic-fused 6 member [6,6,5] ring oxazolidinones (6) can be used in conjunction with non-antibacterial agents as is known to those skilled in the art.

Suitable pharmaceutically acceptable salts include, for example, chloride, sulfate, phosphate, citrate and oxylate.

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula CH$_3$—C(=$Z_1$)H. Groups $R_i$ and $R_j$ would represent monovalent variable substituents if attached to the formula CH$_3$—CH$_2$—C($R_i$)($R_j$)H$_2$. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom.

Chemical formulas or portions thereof drawn in a linear fashion represent atoms in a linear chain. The symbol "—" in general represents a bond between two atoms in the chain. Thus $CH_3$—O—$CH_2$—CH-($R_i$)—$CH_3$ represents a 2-substituted-1-methoxypropane compound. In a similar fashion, the symbol "=" represents a double bond, e.g., $CH_2$=C($R_i$)—O—$CH_3$, and the symbol "≡" represents a triple bond, e.g., HC≡C—CH($R_i$)—$CH_2$—$CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by N*=C($CH_3$)—CH=CCl—CH=C*H with the convention that the atoms marked with an asterisk (*) are bonded to each other resulting in the formation of a ring. Likewise, the cyclic molecular fragment, 4-(ethyl)-1-piperazinyl can be represented by —N*—($CH_2$)$_2$—N($C_2H_5$)—$CH_2$C*$H_2$.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, —C($X_1$)($X_2$)— the two substituents may be in either an axial or equatorial position relative to the ring and may change between axial-/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent ($X_2$) will be identified as being in the alpha ($\alpha$) configuration and is identified by a broken, dashed or dotted line attachment to the carbon atom, i.e., by the symbol "— — —" or "...". The corresponding substituent attached "above" ($X_2$) the other ($X_1$) is identified as being in the beta ($\beta$) configuration and is indicated by an unbroken line attachment to the carbon atom.

When a variable substituent is bivalent, the valences may be taken together or separately or both in the definition of the variable. For example, a variable $R_i$ attached to a carbon atom as —C(=$R_i$)— might be bivalent and be defined as oxo or keto (thus forming a carbonyl group (—CO—) or as two separately attached monovalent variable substituents $\alpha$—$R_{i\text{-}j}$ and $\beta$—$R_{i\text{-}k}$. When a bivalent variable, $R_i$, is defined to consist of two monovalent variable substituents, the convention used to define the bivalent variable is of the form "$\alpha$—$R_{i\text{-}j}$:$\beta$—$R_{i\text{-}k}$" or some variant thereof. In such a case both $\alpha$—$R_{i\text{-}j}$ and $\beta$—$R_{i\text{-}k}$ are attached to the carbon atom to give —C($\alpha$—$R_{i\text{-}j}$)($\beta$—$R_{i\text{-}k}$)—. For example, when the bivalent variable $R_6$, —C(=$R_6$)— is defined to consist of two monovalent variable substituents, the two monovalent variable substituents are $\alpha$-$R_{6\text{-}1}$:$\beta$-$R_{6\text{-}2}$, ... $\alpha$-$R_{6\text{-}9}$:$\beta$-$R_{6\text{-}10}$, etc, giving -C($\alpha$-$R_{6\text{-}1}$)($\beta$-$R_{6\text{-}2}$)-, ... -C($\alpha$-$R_{6\text{-}9}$)($\beta$-$R_{6\text{-}10}$)-, etc. Likewise, for the bivalent variable $R_{11}$, —C(=$R_{11}$)—, two monovalent variable substituents are $\alpha$-$R_{11\text{-}1}$:$\beta$-$R_{11\text{-}12}$. For a ring substituent for which separate $\alpha$ and $\beta$ orientations do not exist (e.g. due to the presence of a carbon carbon double bond in the ring), and for a substituent bonded to a carbon atom which is not part of a ring the above convention is still used, but the $\alpha$ and $\beta$ designations are omitted.

Just as a bivalent variable may be defined as two separate monovalent variable substitutents, two separate monovalent variable substituents may be defined to be taken together to form a bivalent variable. For example, in the formula —$C_1$($R_i$)H—$C_2$($R_j$)H—0 ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation "... $R_i$ and $R_j$ are taken together to form —$CH_2$—$CH_2$—O—CO—..." means a lactone in which the carbonyl is bonded to $C_2$. However, when designated "... $R_j$ and $R_i$ are taken together to form —CO—O—$CH_2$—$CH_2$— the convention means a lactone in which the carbonyl is bonded to $C_1$.

The carbon atom content of variable substituents is indicated in one of two ways. The first method uses a prefix to the entire name of the variable such as "$C_1$-$C_4$", where both "1" and "4" are integers representing the minimum and maximum number of carbon atoms in the variable. The prefix is separated from the variable by a space. For example, "$C_1$-$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$-$C_4$ alkoxycarbonyl describes a group $CH_3$—($CH_2$)$_n$—O—CO— where n is zero, one or two. By the second method the carbon atom content of only each portion of the definition is indicated separately by enclosing the "$C_i$-$C_j$" designation in parentheses and placing it immediately (no intervening space) before the portion of the definition being defined. By this optional convention ($C_1$-$C_3$)alkoxycarbonyl has the same meaning as $C_2$-$C_4$ alkoxycarbonyl because the "$C_1$-$C_3$" refers only to the carbon atom content of the alkoxy group. Similarly while both $C_2$-$C_6$ alkoxyalkyl and ($C_1$-$C_3$)alkoxy($C_1$-$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

The oxazolidinones of the present invention have different positional numbering systems depending on which nomenclature method is used, see CHART F. CHART F shows the correlation of the IUPAC (Chemical Abstracts Nomenclature) with a simplified positional nomenclature system. The nomenclature system used in this patent is the IUPAC system.

II. DEFINITIONS

All temperatures are in degrees Centigrade.
TLC refers to thin-layer chromatography.
Saline refers to an aqueous saturated sodium chloride solution.
DDQ refers to 2,3-dichloro-5,6-dicyano-1,4-benzoquinone.
LDA refers to lithium diisopropylamide.
CBZ refers to carbobenzyloxy.
IR refers to infrared spectroscopy.

CMR refers to C-13 magnetic resonance spectroscopy, chemical shifts are reported in ppm (δ) downfield from TMS.

NMR refers to nuclear (proton) magnetic resonance spectroscopy, chemical shifts are reported in ppm (δ) downfield from tetramethylsilane.

φ refers to phenyl ($C_6H_5$).

MS refers to mass spectrometry expressed as m/e or mass/charge unit. [M+H]+ refers to the positive ion of a parent plus a hydrogen atom. EI refers to electron impact. CI refers to chemical ionization. FAB refers to fast atom bombardment.

Ether refers to diethyl ether.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1

(±) Methyl indoline-2-carboxylate (II)

Magnesium turnings (3.60 g) are added to a mixture of ethyl indole-2-carboxylate (I, Aldrich Chemical, 13.963 g) in methanol (200 ml). After evolution of gas has started, the mixture is placed in an ice bath and the temperature kept below 45°. After 4.5 hours all of the magnesium is used up and the temperature is 7°. At this time the mixture is added to ice cold hydrochloric acid (3N, 120 ml). The acidic mixture is then made alkaline (pH 10) with ammonium hydroxide (3N). The mixture is then extracted with methylene chloride (3 x). The combined organic layers are dried over magnesium sulfate and concentrated to give the title compound.

EXAMPLE 2

(±) Methyl indoline-2-carboxylate (II)

Magnesium turnings (6.449 g) are added to a suspension of ethyl indole-2-carboxylate (I, Aldrich, 25.083 g) in methanol (freshly opened, HPLC grade, 350 ml). The mixture is stirred at 24° for 10 minutes, then placed in an ice bath. After stirring for 15 minutes in the ice bath, there is much gas evolution and the temperature rises to 35° but then subsides to 0° within one hour. After stirring for another two hours at 0°, cold hydrochloric acid (3N, 250 ml) is added slowly. The mixture turns to a gel. The gel is then treated with ammonium hydroxide (3N, 250 ml). Upon adding methylene chloride to the gel, it forms an inseparable suspension. The crude mixture is made acidic (pH 1) with aqueous sodium bisulfate (10%) then made alkaline (pH 8-9) with ammonium hydroxide (3N). This mixture is then extracted with methylene chloride. The combined organic layers are dried over magnesium sulfate and concentrated to provide a mixture of an oil with some solid. From this mixture an off white solid is obtained by washing the mixture with ethyl acetate/hexane (25/75). A small sample (620 mg) of the recovered oil is purified by passing it over a silica column (20.5×2.5 cm, 40–63 μ). The column is eluted with ethyl acetate/hexane (⅓, 1l; 1/1, 0.5l) collecting 25 ml fractions. The appropriate fractions are pooled and concentrated to give the title compound, NMR ($CDCl_3$, 300 MHz) 7.04, 6.71, 4.46, 4.37, 3.74 and 3.35 δ; CMR ($CDCl_3$, 75.47 MHz) 33.69, 52.42, 59.81, 110.05, 119.48, 124.45, 126.63, 127.67, 150.03 and 174.62 δ; IR ($CHCl_3$) 3480, 3390, 2970, 1730, 1605, 1480, 1460, 1430 and 1200 $cm^{-1}$; MS (m/e) 177, 147, 129, 119, 118, 117, 91, 86, 84 and 49, exact mass calcd for $C_{10}H_{11}NO_2$ (177.0790), found 177.0789; TLC (ethyl acetate/hexane, 1/1) $R_f$=0.55 (UV).

EXAMPLE 3

(±) Methyl (1-benzyloxycarbonyl)indoline-2-carboxylate (III)

Sodium bicarbonate (15.825 g) is added to a solution of (±) methyl indoline-2-carboxylate (II, EXAMPLE 2, 16.055 g) in acetone/water (50/50, 100 ml) while stirring at 0°. Benzyl chloroformate (14.5 ml) is added to this mixture causing much effervescence. After stirring for 3 hours the mixture is added to ether (160 ml) and the layers are separated. The organic layer is washed with aqueous sodium bisulfate (10%, 4×50 ml) and aqueous sodium carbonate (10%, 3×50 ml). The organic layer separated, then dried over sodium sulfate and concentrated under reduced pressure to give the title compound as a crude solid. A small sample of the solid (470 mg) is purified by flash column chromatography on silica gel (16 cm×2.5 cm, 40–63μ silica) eluting with ethyl acetate/hexane (25/75). The appropriate fractions are pooled and concentrated to give the title compound, NMR ($CDCl_3$, 300 MHz) 7.95, 7.37–6.94, 5.30, 5.13, 4.93, 3.73, 3.50 and 3.12 δ; CMR ($CDCl_3$, 75.47 MHz) 32.67, 52.15, 59.84, 67.03, 114.60, 122.84, 124.20, 127.78, 127.88, 128.03, 128.32, 135.6, 141.7, 151.9 and 171.8 δ; IR ($CHCl_3$) 2920, 1750–1690, 1600, 1480, 1400, 1260 and 1040 $cm^{-1}$; MS (m/e) 311 (20.98), 252, 208, 117, 91, 65, exact mass calcd for $C_{18}H_{17}NO_4$ (311.1157), found 311.1169; TLC (ethyl acetate/hexane, 1/1) $R_f$=0.62.

EXAMPLE 4

(±) 1-Benzyloxycarbonyl-2-hydroxymethylindoline (IV)

Lithium borohydride (7.061 g) is added to a solution of (±) methyl (1-benzyloxycarbonyl)indoline-2-carboxylate (III, EXAMPLE 3, 26.510 g) in freshly distilled tetrahydrofuran (250 ml). The mixture becomes very effervescent and changes color. The mixture is then cooled in an ice bath and stirred under nitrogen for 20.5 hours and allowed to warm to 20°–25°. The mixture is then cooled to 0° and glacial acetic acid (30 ml) is added over ten minutes. The mixture is very effervescent upon adding the glacial acetic acid. After the final addition of acid, ethyl acetate (200 ml) and saturated aqueous sodium bicarbonate (25 ml) are added. The layers are then separated and the organic layer is washed with additional saturated aqueous sodium bicarbonate (4×100 ml) and saline. The organic layer is dried over magnesium sulfate and concentrated to provide an oil which solidifies overnight. This product is combined with 5.895 g (ca. 90% pure) from an earlier lot and purified by passing the combination over a siliga gel column (9 cm×6.5 cm, 63–200μ) eluting with ethyl acetate/hexane (⅙.5 l, 1/1 1.9 l) collecting 50 ml fractions. The appropriate fractions are pooled and concentrated to give the title compound. An analytical sample is obtained by recrystallization from ethyl acetate, mp 89°–90°; NMR (CH$_3$OD, 300 MHz) 7.30, 7.14, 6.94, 5.25, 4.50, 3.67, 3.54, 3.25 and 3.00 δ; CMR (CH$_3$OD, 75.47 MHz) 31.88, 61.75, 63.73, 68.4, 116.28, 124.21, 126.01, 128.16, 129.28, 129.24, 129.67, 131.6, 137.3, 142.7 and 154.2 δ; IR (CHCl$_3$) 3600, 3460, 2920, 1690, 1600, 1480, 1400, 1280, 1200 and 1040 cm$^{-1}$; MS (m/e) 283, 252, 208, 130, 118, 92, 91, 77, 65, 51 and 38, exact mass calcd for C$_{17}$H$_{17}$NO$_3$ (283.1208), found 283.1200.

EXAMPLE 5

(±) 1-Benzyloxycarbonylindoline-2-carboxaldehyde (V)

Dimethyl sulfoxide (2.75 ml) is added to a solution of oxalyl chloride (1.7 ml) in methylene chloride (45 ml) at −78° under nitrogen via cannula over six minutes. After 20 minutes, (±) 1-benzyloxycarbonyl-2-hydroxymethylindoline (IV, EXAMPLE 4, 5.003 g) in methylene chloride (20 ml) is added via cannula over 12 minutes. The mixture is stirred for 30 minutes, then triethyl amine (7.40 ml) is added. The mixture is stirred at −78° for an additional 20 minutes then stirred at 20°–25° for one hour, then poured into water (50 ml) and the layers are separated. The aqueous layer is extracted with methylene chloride (5×20 ml). The combined organic layers are washed sequentially with saline, hydrochloric acid (3N, 100 ml), water (100 ml), aqueous sodium carbonate (5%, 100 ml) and again with water (100 ml). The organic layer is then dried over magnesium sulfate and concentrated under reduced pressure to give an oil. The oil is passed over a silica column (27.5 cm×4.0 cm, 40–63 mm) and is eluted with ethyl acetate/hexane (1/5.6 300 ml, ½ l), collecting 29 ml fractions. The appropriate fractions are pooled and concentrated to give the title compound, NMR (CDCl$_3$, 300 MHz) 9.62, 7.93, 7.34, 7.20, 7.11, 6.97, 5.23, 4.82, 3.36 and 3.13 δ; CMR (CDCl$_3$, 75.47 MHz) 29.74, 65.76, 67.57, 115.05, 123.34, 124.64, 128.08, 128.20, 128.40, 128.61, 135.57, 141.7, 151.9 and 198.73 δ; IR (CHCl$_3$) 2940, 1700, 1600, 1480, 1400, 1320, 1270-1190 and 1030 cm$^{-1}$; MS (m/e) 281, 252, 208, 117, 91 and 65, exact mass calcd for C$_{17}$H$_{15}$NO$_3$ (281.1052), found 281.1066; TLC (ethyl acetate/hexane, ⅓) R$_f$=0.28.

EXAMPLE 6

(±)
1-Benzyloxycarbonyl-2-(1-cyano-1-hydroxymethyl)indoline (VI, diastereomers A [RS,SR-cis] and B [RR,SS-trans])

Acetone cyanohydrin (1.27 ml) is added to a solution of (±) 1-benzyloxycarbonylindoline-2-carboxaldehyde (V, EXAMPLE 5, 3.935 g) in methanol (85 ml), under nitrogen. Potassium carbonate (0.165 g) is added to this mixture. The mixture is stirred for three days. After this time, the mixture is added to ethyl acetate (50 ml) and washed with saline (50 ml). The aqueous wash is then extracted with ethyl acetate (2×25 ml). The combined organic layers are concentrated under reduced pressure to provide a mixture of the diastereomers A and B. The diastereomeric mixture is placed on a silica gel column (48.5 cm×6.5 cm, 63–200μ) eluting with ethyl acetate/hexane (⅛, 8.7 l: 1/1, 2 l). The appropriate fractions are pooled. The earlier fractions provided almost pure diastereomer A from which pure diastereomer A is obtained by crystallization, NMR (CDCl$_3$, 300 MHz) 7.30, 7.08, 6.93, 5.26, 4.69, 3.41 and 2.94 δ; CMR (CDCl$_3$, 75.47 MHz) 30.60, 62.57, 66.2, 68.81, 115.62, 117.30, 123.41, 123.88, 124.71, 127.92, 128.21, 128.38, 128.65, 128.74 and 135.05 δ; IR (CHCl$_3$) 3700, 3320, 2950, 1670, 1600, 1480, 1400, 1325, 1290, 1140, 1080, 1040 and 1020 cm$^{-1}$; MS (m/e) 308, 281, 252, 208, 162, 147, 130, 118, 117, 91, 77, 65, 51 and 40; exact mass calcd for C$_{18}$H$_{16}$N$_2$O$_3$ (308.1161), found 308.1158; TLC (ethyl acetate/hexane, ⅓) R$_f$=0.26.

Later fractions provide a mixture of diastereomers comprised mostly of diastereomer B. This mixture is chromatographed on a silica colum (38.5 cm×5.5 cm, 40–63μ) eluting with ethyl acetate/hexane (1/9, 1 l; ¼, 5 l; 1/1, 1 l). The appropriate fractions are pooled and concentrated. The concentrate was crystallized to give pure diastereomer B, NMR (CDCl$_3$, 300 MHz) 7.40, 7.18, 7.02, 5.32, 4.84, 4.71, 3.46 and 3.10 δ; CMR (CDCl$_3$, 75.47 MHz) 30.27, 61.26, 63.76, 68.38, 115.79, 117.62, 123.80, 124.80, 127.78, 128.10, 128.39, 128.49, 128.69 and 134.88 δ; IR (CHCl$_3$) 3600, 3400, 2960, 1670, 1600, 1480, 1400, 1320, 1285, 1135, 1080, 1040 and 1020 cm$^{-1}$; MS (m/e) 281, 252, 208, 162, 146, 130, 118, 117, 103, 91, 77, 65, 51 and 38; exact mass calcd for C$_{18}$H$_{16}$N$_2$O$_3$ (308.1161), found 308.1147; TLC (ethyl acetate/hexane, ⅓) R$_f$=0.18.

EXAMPLE 7

(±)
1-Benzyloxycarbonyl-2-(1-hydroxy-2-aminoethyl)-indoline (VII, diastereomer B [RR,SS-trans])

Borane-dimethylsulfide (2M, 0.85 ml) is added to a mixture of (±) 1-benzyloxycarbonyl-2-(1-cyano-1-hydroxymethyl)indoline [VI diastereomer B, EXAMPLE 6, 0.431 g] in refluxing tetrahydrofuran (5 ml) slowly over 6 minutes. After one hour additional borane-dimethyl sulfide (2M, 0.5 ml) is added over 2 minutes. The mixture is continued to stir at reflux for 30 minutes then hydrochloric acid (3N, 1.8 ml) is added slowly with much effervescence over 2 minutes. The mixture is stirred for 15 minutes at reflux then cooled to 0° in an ice bath and sodium hydroxide (5N, 1.6 ml) is added slowly over 2 minutes. The solvent layers are separated and the aqueous layer is saturated with potassium carbonate and extracted with ethyl acetate (4×, 30 ml total). The organic layers are combined, dried over magnesium sulfate and then concentrated to give the title compound, NMR (methanol-d$_4$, 300 MHz) 7.35, 7.15, 6.96, 5.26, 4.64, 3.87, 3.22, 3.03 and 2.43 δ; CMR (methanol-d$_4$, 75.47 MHz) 30.5, 62.90, 68.8, 117.2, 124.48, 125.8, 128.24, 129.34, 129.68, 132.9 and 138.1 δ.

EXAMPLE 8

(±)
1-Benzyloxycarbonyl-2-(1-hydroxy-2-N-acetylaminoethyl)indoline(VIII, diastereomer B)

Acetic anhydride (2.0 ml) is added to a mixture of (±) 1-benzyloxycarbonyl-2-(1-hydroxy-2-amino)-ethyl)indoline (VII, diastereomer B, EXAMPLE 7, 1.758 g)

in ethylacetate (5 ml). The mixture is stirred for 1.25 hours and then concentrated to an oil. The oil is then passed over a silica column (30.0×5.5 cm, 40–63μ) eluting with ethyl acetate (2.8 l), methanol/ethyl acetate (2.5/97.5, 2.5 l), methanol/ethyl acetate (10/90, 2 l) and methanol/ethyl acetate (20/80, 1 l) while collecting 50 ml fractions. The appropriate fractions are pooled and concentrated to give the title compound, NMR (methanol-d$_4$, 300 MHz) 7.64–7.27, 7.13, 6.93, 5.26, 4.61, 3.97, 3.26–3.04 and 1.87 δ; CMR (methanol-d$_4$, 75.47 MHz) 22.57, 30.60, 42.3, 62.83, 68.8, 72.4, 117.2, 124.49, 125.71, 128.29, 129.28, 129.33, 129.68, 132.9, 138.2, 143.8 and 174.3 δ; IR (Neat, KRS-5 crystal, 3300, 1690, 1650, 1480, 1400, 1270 and 1130 cm−1; MS (m/e) 354, 336, 277, 253, 208, 186, 162, 143, 130, 118, 103, 102, 91, 60 and 43; exact mass calcd for $C_{20}H_{22}N_2O_4$ (354.1579), found 354.1597; TLC (ethyl acetate) $R_f$=0.19.

EXAMPLE 9

(±) 1-Benzyloxycarbonyl-2-(1-acetoxy-2-N-acetylaminoethyl)indoline (XII, diastereomer B,[SS,RR-trans)]

Acetic anhydride (0.5 ml) is added to a mixture of (±) 1-benzyloxy carbonyl-2-(1-hydroxy-2-amino)-ethyl)indoline (VII diastereomer B, EXAMPLE 7, 138 mg) in pyridine (1 ml) at 0°. The mixture is stirred for 7 minutes then concentrated under reduced pressure. Subsequent purification by chromatography provides the title compound, NMR (methanol-d$_6$, 300 MHz) 7.60–7.32, 7.16, 6.98, 5.28, 5.17, 4.73, 3.40–2.94, 1.84 and 1.80 δ; CMR (methanol-d$_6$, 75.47 MHz) 20.58, 22.43, 31.92, 40.02, 40.37, 60.70, 61.57, 68.77, 74.68, 116.97, 124.21, 124.60, 125.60, 128.13, 128.42, 129.16, 129.28, 129.41, 129.68, 137.52, 172.05 and 173.52 δ; MS (m/e) 396, 336, 277, 208, 159, 118, 102, 91, 60 and 43; exact mass calcd for $C_{22}H_{24}N_2O_5$ (396.1685), found 396.1692; TLC (ethyl acetate) $R_f$=0.27.

EXAMPLE 10

(±) 2-(1-Hydroxy-2-N-acetylaminoethyl)indoline (IX, diastereomer B [SS,RR-trans])

A mixture of (±) 1-benzyloxycarbonyl-2-(1-hydroxy-2-N-acetylaminoethyl)-indoline (VIII diastereomer B, EXAMPLE 8, 725 mg) and palladium on carbon (10%, 225 mg) is stirred in ethyl acetate (125 ml) under hydrogen for 19 hours. After this time, the mixture is filtered over diatomaceous earth and concentrated to provide crude product as an oil. The oil is purified by passing it over a silica column (22 cm×2.5 cm, 40–63μ) eluting with ethyl acetate (840 ml) and methanol/ethyl acetate (10/90, 1 l) while collecting 24 ml fractions. The appropriate fractions are pooled and concentrated to provide the title compound, NMR (methanol-d$_4$, 300 MHz) 7.01, 6.93, 6.62, 3.72, 3.57, 3.44, 3.17–2.99, 2.84 and 1.96 δ; CMR (methanol-d$_4$, 75.47 MHz) 22.64, 33.36, 44.19, 63.32, 73.93, 110.87, 119.86, 125.46, 128.28, 130.09, 152.38 and 173.81 δ; IR (CHCl$_3$) 3440, 2980, 1660, 1600, 1480, 1460 and 1200 cm−1; MS (m/e) 220, 143, 130, 119, 118, 117, 103, 91, 60 and 42; exact mass calcd for $C_{12}H_{16}N_2O_2$ (220.1212), found 220.1208.

EXAMPLE 11

(±) (1S,9aS/1R,9aR) N-[(9,9a-Dihydro-3-oxo-1H,3H-oxazolo[3,4-a]indol-1-yl)methyl]acetamide (X, diastereomer B, [SS,RR-trans])

Method A

Phosgene in toluene (1.93M, 90 μl) is added to a mixture of (±) 2-(1-hydroxy-2-N-acetylaminoethyl)indoline (IX diastereomer B, EXAMPLE 10, 32 mg) in dry methylene chloride (4 ml) at −15°. The mixture is stirred for 45 minutes then saturated aqueous sodium bicarbonate (3.0 ml) is added. The solvent layers are separated and the aqueous layer is extracted with methylene chloride (3×). The combined organic layers are washed with aqueous sodium bisulfate (10%, 3 ml), saline (3 ml) and then dried over magnesium sulfate and concentrated to provide the title compound as an oil. The oil is then purified on a 1000μ silica prep plate by developing in methanol/methylene chloride (5/95, 5×) to provide the title compound.

Method B

Sodium hydroxide (5N, 1 ml) is added to a solution of (±) bis acetylated 1-benzyloxycarbonyl-2-(1-acetoxy-2-N-acetylaminoethyl)-indoline (XII, EXAMPLE 9, 10 mg) in absolute ethanol (1 ml). The mixture is stirred and after one hour additional sodium hydroxide (5N, 0.25 ml) is added. The mixture is then stirred for an additional 1.5 hours and then sodium hydroxide (5N, 0.5 ml) is added again. This mixture is then stirred for 26.5 hours and then extracted with methylene chloride (3×, 20 ml total). The combined organic layers are dried over magnesium sulfate and concentrated to provide the title compound.

Method C

A mixture of (±) 1-benzyloxycarbonyl-2-(1-hydroxy-2-N-acetylaminoethyl)indoline (VIII diastereomer B, EXAMPLE 8, 17 mg) in sodium hydroxide (0.003M in 75% aqueous ethanol, 1.9 ml) is stirred for 3 days. The mixture is then extracted with methylene chloride (3×). The organic extracts are combined, washed with saline (2×), then dried over magnesium sulfate and concentrated to an oil, NMR (CDCl$_3$, 300 MHz) 7.40, 7.24, 7.11, 6.31, 4.62, 4.50, 3.78, 3.69, 3.29, 3.11 and 2.07 δ; CMR (CDCl$_3$, 75.47 MHz) 23.12, 34.94, 41.41, 61.81, 82.64, 115.27, 125.08, 125.35, 128.21, 132.12, 140.14, 155.79 and 170.97 δ; IR (CDCl$_3$) 3440, 2980, 1750, 1670, 1600, 1470, 1370, 1260, 1120 and 1050 cm−1; MS (m/e) 246, 202, 187, 174, 159, 143, 130, 118, 117, 103, 85, 73, 43, 30 and 28, exact mass calcd for $C_{13}H_{14}N_2O_3$ (246.1004), found 246.1002; TLC (ethyl acetate) $R_f$=0.15.

EXAMPLE 12

(±) (1S,9aS/1R,9aR) N-[(7-acetyl-9,9a-dihydro-3-oxo-1H,3H-oxazolo[3,4-a]indol-1-yl)methyl]acetamide (XI, diastereomer B, [SS,RR-trans])

A mixture of (±) (1S,9aS/1R,9aR) N-[(9,9a-dihydro-3-oxo-1H,3H-oxazolo[3,4-a]indol-1-yl)methyl]acetamide (X diastereomer B, EXAMPLE 11, 8 mg), methane sulfonic acid (0.5 ml), and acetic anhydride (10 μl) is stirred in methylene chloride (0.2 ml) from 0° to 20° for 19.5 hours. After this time the mixture is cooled in an ice bath and additional acetic anhydride (10 µl) is added. The mixture is stirred for one hour then added to a small amount of ice and saturated aqueous sodium bicarbonate (7 ml) is added, then solid sodium bicarbonate is added until alkaline. The mixture is then extracted with methylene chloride (5×, 20 ml total). The combined extract layers provide 8 mg of material. The 8 mg is then purified by chromatography (5 cm×0.5 cm disposable pipet, 40–63 µ silica) eluting with 1% and 2.5% methanol/methylene chloride gradient while collecting 0.4 ml fractions. The appropriate fractions are pooled and concentrated to provide the title compound.

EXAMPLE 13

(±) (1S,9aS/1R,9aR) N-[(7-acetyl-9,9a-dihydro-3-oxo-1H,3H-oxazolo[3,4-a]indol-1-yl)methyl]acetamide (XI, diastereomer B, [SS,RR-trans])

Acetic anhydride (91 µl) is added to a mixture of (±) (1S,9aS/1R,9aR) N-[(9,9a-dihydro-3-oxo-1H,3H-oxazolo[3,4-a]indol-1-yl)methyl]acetamide (X diastereomer B, EXAMPLE 11, 74 mg) in methane sulfonic acid (1 ml) at 0° over 1 minute. The mixture is stirred for 20.5 hours and allowed to warm to 20°–25° during this time. At the end of this time, a small amount of ice is added and the mixture is diluted with methylene chloride. To this mixture of sodium bicarbonate (2.4 g) is added slowly. The solvent layers are separated and the aqueous layer is extracted with additional methylene chloride (7×1 ml). The combined organic layers are dried over magnesium sulfate and concentrated to provide an oil. This oil is purified on a silica preparative plate (1000µ) by developing it in methanol/methylene chloride (5/95, 3×) which provides the title compound, NMR (CDCl$_3$, 300 MHz) 7.88, 7.84, 7.43, 6.40, 4.62, 4.57, 3.75, 3.36, 3.13, 2.58 and 2.08 δ; CMR (CDCl$_3$, 75.47 MHz) 23.15, 26.62, 34.24, 41.02, 61.84, 83.26, 114.37, 125.53, 129.86, 132.98, 134.2, 144.1, 154.7, 170.6 and 196.5 δ; IR (CHCl$_3$) 3660, 3440, 2980, 2920, 1760, 1670, 1600, 1480, 1420, 1350, 1260, 1120, 1050, 980 and 700 cm$^{-1}$; MS (m/e) 288, 244, 229, 216, 201, 185, 170, 160, 144, 130, 118, 85, 73 and 43, exact mass calcd for C$_{15}$H$_{16}$—N$_2$O$_4$ (288.1110), found 288.1105.

EXAMPLE 14

(±) 1-Benzyloxycarbonyl-2-(1-hydroxy-2-aminomethyl)indoline (VII, diastereomer A, [RS,SR-cis])

Borane-dimethylsulfide (2M, 2.6 ml) is added to a mixture of (±) 1-benzyloxycarbonyl-2-(1-cyano-1-hydroxymethyl)indoline [VI(>95% diastereomer A), EXAMPLE 6, 848 mg] in freshly distilled tetrahydrofuran (10 ml) at reflux over 15 minutes. The mixture is stirred at reflux for 2 hours then hydrochloric acid (3N, 3.2 ml) is added over 2 minutes. After stirring for 10 minutes, the mixture is cooled to 0° and sodium hydroxide (5N, 3 ml) is added. The mixture is stirred for 30 minutes then saline and methylene chloride is added. The solvent layers are separated and the aqueous layer is extracted with additional methylene chloride (4×). The combined organic layers are washed with saline, dried over magnesium sulfate, and concentrated to provide the title compound, NMR (methanol-d$_4$, 300 MHz) 5.27, 4.47 and 3.86 δ.

EXAMPLE 15

(±) 1-Benzyloxycarbonyl-2-(1-hydroxy-2-N-acetylaminoethyl)indoline (VIII, diastereomer A, [RS,SR-cis])

Acetic anhydride (1.0 ml) is added to a mixture of (±) 1-benzyloxycarbonyl-2-(1-hydroxy-2-aminoethyl)indoline (VII diastereomer A, EXAMPLE 14, 780 mg) in ethyl acetate (30 ml) at 0°. The mixture is stirred at 0° for one hour then at 20°–25° for 3.5 hours. The mixture is concentrated to a white solid (784 mg). The solid is dissolved in chloroform and passed over a silica column (4.5×19 cm, 40–63µ), eluted with ethyl acetate (2 L), methanol/ethyl acetate (2.5/97.5, 2 l), and methanol/ethyl acetate (5/95, 1 l) while collecting 30 ml fractions. The appropriate fractions are pooled and concentrated to give the title compound, NMR (methanol-d$_4$, 300 MHz) 7.36, 7.10, 6.92, 5.25, 4.49, 4.08, 3.32, 3.15 and 1.88 δ; CMR (methanol-d$_4$, 75.47 MHz) 22.6, 29.13, 42.98, 62.7, 68.3, 71.4, 116.3, 124.01, 125.2, 127.78, 129.19, 129.57, 132.5, 137.1 and 173.3 δ; IR (mineral oil mull) 3495, 3317, 2924, 1686, 1650, 1600, 1552, 1487, 1463, 1422, 1307, 1144 and 1050 cm$^{-1}$; MS (m/e) 354,, 336, 277, 253, 233, 208, 186, 159, 143, 130, 118, 102, 91, 60 and 43; exact mass calcd for C$_{20}$H$_{22}$N$_2$O$_4$ (354.1579), found 354.1582; TLC (ethyl acetate) R$_f$=0.23.

EXAMPLE 16

(±) 2-(1-Hydroxy-2-N-acetylaminoethyl)indoline (IX, diastereomer A, [RS,SR-cis])

A mixture of (±) 1-benzyloxycarbonyl-2-(1-hydroxy-2-N-acetylamino-ethyl)indoline (VIII diastereomer A, EXAMPLE 15, 410 mg) and palladium on carbon (10%, 130 mg) is stirred in methanol (82 ml) under hydrogen for one hour. The mixture is then filtered over diatomaceous earth and concentrated to the title compound, NMR (methanol-d$_4$, 300 MHz) 7.00, 6.93, 6.61, 3.67, 3.35, 3.10, 2.89 and 1.97 δ; CMR (methanol-d$_4$, 300 MHz) 22.57, 33.83, 43.93, 63.14, 74.93, 110.60, 119.76, 125.44, 128.20, 130.08, 152.51 and 173.97 δ; IR (mineral oil mull, 3305, 2924, 1637, 1610, 1551 and 1488 cm$^{-1}$; MS (m/e) 220, 159, 143, 130, 118, 103, 91, 60 and 43; exact mass calcd for C$_{12}$H$_{16}$N$_2$O$_2$ (220.1212), found 220.1206; TLC (ethyl acetate) R$_f$=0.10.

EXAMPLE 17

(±) 2-(1-Hydroxy-2-N-acetylaminoethyl)-1-chlorocarbonylindoline(IX', diastereomer A, [RS,SR-cis])

Phosgene (1.93M, in toluene, 0.65 ml) is added to a mixture of (±) 2-(1-hydroxy-2-N-acetylaminoethyl)indoline (IX diastereomer A, EXAMPLE 16, 230 mg) in dry methylene chloride (20 ml) at −15° under nitrogen. After 50 minutes the mixture is added to saturated aqueous bicarbonate (5 ml). The solvent layers are separated. The aqueous layer is extracted with methylene chloride (3×50 ml). The combined organic layers are washed with saline (2×60 ml), dried over magnesium sulfate, and then concentrated to give the title compound, NMR (methanol-d$_4$, 300 MHz) 7.72, 7.18, 7.08, 4.70, 4.28, 3.37, 3.21 and 1.96 δ; CMR (methanol-d$_4$, 75.47 MHz) 22.43, 28.58, 42.74, 66.85, 72.24, 117.12, 125.61, 126.16, 127.86, 134.30, 142.9, 145.4 and 173.1 δ; IR (KRS-5 crystal, 1740, 1660, 1560, 1490, 1470, 1380 and 1280 cm$^{-1}$; MS (EI, m/e; it spontaneously closes to give (X)) 246, 205, 187, 174, 158, 143, 130, 118, 102, 85, 73 and 60, 42, exact mass calcd for C$_{13}$H$_{14}$N$_2$O$_3$ (246.1004), found 246.1009; MS (FAB, m/e) 285 and 283, exact mass calcd for C$_{13}$H$_{16}$ClN$_2$O$_3$ (283.0849), found 283.0868; TLC (ethyl acetate) R$_f$=0.20.

EXAMPLE 18

(±) (1S,9aS/1R,9aR)
N-[(9,9a-Dihydro-3-oxo-1H,3H-oxazolo[3, 4-a]indol-1-yl)methyl]acetamide (X, diastereomer A, [RS,SR-cis])

(±) 2-(1-Hydroxy-2-N-acetylaminoethyl)-1-chlorocarbonylindoline (IX', diastereomer A, EXAMPLE 17, 32 mg) in methanol (2 ml) at 0° is combined with triethylamine (0.10 ml). After 15 min the mixture is concentrated under reduced pressure and taken up in ethyl acetate (2 ml) and water (1 ml). This mixture is washed with hydrochloric acid (1N, 1 ml). The organic layer is then washed with saturated aqueous sodium bicarbonate (1 ml) and then saline (1 ml). The organic layer is dried over magnesium sulfate and concentrated under reduced pressure to give the title compound, NMR (methanon-d$_4$, 300 MHz) 7.31, 7.23, 7.09, 5.00, 3.61, 3.45, 3.33, 3.05 and 1.84 δ; CMR (methanol-d$_4$, 75.47 MHz) 22.34, 30.56, 41.13, 62.87, 78.66, 116.08, 126.06, 126.65, 128.83, 134.67, 141.62, 158.10 and 173.56 δ; MS (m/e) 246, 187, 143, 130, 118,85, 42; exact mass calcd for C$_{13}$H$_{14}$N$_2$O$_3$ (246.1004), found 246.1001.

EXAMPLE 19

(±) (1S,9aS/1R,9aR)
N-[(7-Acetyl-9,9a-dihydro-3-oxo-1H,3H-oxazolo-[3,4-a]indol-1-yl)methyl]acetamide (XI, diastereomer A, [RS,RS-cis])

Acetic anhydride (53 μl) is slowly added to a mixture of (±) N-[(9,9a-dihydro-3-oxo-1H,3H-oxazolo[3,4-a]indol-1-yl)methyl]acetamide (X diastereomer A, EXAMPLE 18, 21 mg), methanesulfonic anhydride (33 mg) in methylene chloride (0.1 ml) and methane sulfonic acid (0.50 ml) at 0°. The temperature is kept below 15° for 3 hr, then allowed to warm slowly to 20°-25° overnight. Then the mixture is added to crushed ice (0.5 ml). After the ice has melted the mixture is extracted with ethyl acetate (4×3 ml). The combined organic layers are washed with saturated aqueous sodium bicarbonate (2 ml), saline (1 ml), dried over anhydrous potassium carbonate and concentrated to an oil. The oil is place on a silica prepratory plate (14 cm×17.5 cm, 250μ) and developed in methanol/methylene chloride (5/95, 3×). Extraction of the appropriate band and concentration give the title compound.

EXAMPLE 20

(S,S)
1-Benzyloxycarbonyl-2-(1-hydroxy-2-amino)-ethyl)indoline (VII, disatereomer B)

(±) 1-Benzyloxycarbonyl-2-(1-hydroxy-2-amino)ethyl)indoline (VII diastereomer B, EXAMPLE 7) is stirred with (+) or (−) tartaric acid in methylene chloride and then permitted to stand while the product crystallizes out. The crystalline product is obtained by filtration and treated with triethylamine or sodium bicarbonate to obtain the free amine which is obtained by extraction with methylene chloride. The methylene chloride extract is dryed, if necessary, and concentrated to give the title compound.

EXAMPLE 21

(1S,9aS)
N-[(9,9a-Dihydro-3-oxo-1H,3H-oxazolo[3,4-a]indol-1-yl)methyl]acetamide (X, diastereomer B, [SS-trans])

Following the general procedure of EXAMPLES 8, 10 and 11 and making non-critical variations, but starting with (S,S) 1-benzyloxycarbonyl-2-(1-hydroxy-2-amino)-ethyl)-indoline (VII diastereomer B, EXAMPLE 20), the title compound is obtained.

EXAMPLE 22

(1S,9aS)
N-[(7-Acetyl-9,9a-dihydro-3-oxo-1H,3H-oxazolo[3,4-a]indol-1-yl)methyl]acetamide (XI, diastereomer B, [SS-trans])

Following the general procedure of EXAMPLE 12 but starting with (1S,9aS) N-[(9,9a-dihydro-3-oxo-1H,3H-oxazolo[3,4-a]indol-1-yl)methyl]acetamide (X diastereomer B, EXAMPLE 21), the title compound is obtained.

EXAMPLE 23

(1S,10aS/1S,10aR)
[(7-Acetyl-4,9,10,10a-tetrahydro-3-oxo-1H,3H-oxazolo[3,4-a]quinol-1-yl]methyl]acetamide (XIX, diastereomers B/A, [SS,RR-trans/SR,RS-cis])

Following the general procedure of EXAMPLES 1, 3-7, 20, 8 and 10-12 and making non-critical variations but starting with ethyl 1,2,3,4-tetrahydro-2-quinolinecarboxylate, the title compounds are obtained.

EXAMPLE 23A (1S,10aS/1S,10aR)
[(4,9,10,10a-tetrahydro-3-oxo-1H,3H-oxazolo[3,4-a]quinol-1-yl)methyl]acetamide (XIX, diastereomers B/A, [SS,RR-trans/SR,RS-cis])

Following the general procedure of EXAMPLES 1, 3-7, 20, 8, 10 and 11 and making non-critical variations but starting with ethyl 1,2,3,4-tetrahydro-2-quinolinecarboxylate, the title compounds are obtained.

EXAMPLE 24

(±) (1S,9aS/1R,9aR)
N-[(7-bromo-9,9a-dihydro-3-oxo-1H,3H-oxazolo[3,4-a]indol-1-yl)methyl]acetamide (X, diastereomer B).

(±) (1S,9aS/1R,9aR) N-[(9,9a-Dihydro-3-oxo-1H,3H-oxazolo[3,4-a]indol-1-yl)methyl]acetamide (X, diastereomer B, [SS,RR-trans], EXAMPLE 11, 299 mg) is dissolved in acetonitrile (10 ml). To this mixture N-bromosuccinimide (235 mg) and a catalytic amount of benzoylperoxide are added as solids to the mixture at 20°-25°. The mixture is stirred at 20°-25° in a sealed flask over night. Then a small portion is removed and examined by NMR. The mixture was then concentrated under reduced pressure to give the title compound, NMR (CDCl$_3$, 300 MHz) 7.30, 6.49, 4.63, 4.52, 3.72, 3.29, 3.12, 2.76 and 2.06 δ.

EXAMPLE 25

(±) (1S,9aS/1R,9aR)
N-[(7-phenyl-9,9a-dihydro-3-oxo-1H,3H-oxazolo[3,4-a]indol-1-yl)methyl]acetamide (X, diastereomer B)

(±) (1S,9aS/1R,9aR) N-[(7-Bromo-9,9a-dihydro-3-oxo-1H,3H-oxazolo[3,4-a]indol-1-yl)methyl]acetamide (EXAMPLE 24, 129 mg) is dissolved in tetrahydrofuran (1 ml). To this mixture palladium tetrakis(triphenylphosphine) (22 mg), phenylboronic acid (61 mg) and aqueous sodium carbonate (2M, 0.45 ml) is added. The mixture is warmed for 15.5 hours in an oil bath at 68°. The mixture is then partitioned between aqueous sodium carbonate (2M, 2 ml) and methylene chloride (3 ml). After separation of the layers, the aqueous phase is extracted with additional methylene chloride (3×2 ml). The organic layers are combined, dried over magnesium sulfate and concentrated to provide a solid. This solid is taken up in methylene chloride and placed on a 20.5 cm×2.5 cm, 40–63μ silica column and eluted with ethyl acetate/methanol gradient. The appropriate fractions are pooled and concentrated to give the title compound, mp 181°–183°; NMR (CDCl$_3$, 300 MHz) 7.43, 6.08, 4.53, 4.54, 3.83, 3.70, 3.35, 3.17 and 2.07 δ.

EXAMPLES 26–35

OPTICALLY PURE TRICYCLIC-FUSED 5 [6,5,5] MEMBER RING OXAZOLIDINONES (XI)

Following the general procedure of EXAMPLES 24 and 25 and making non-critical variations and (1) using optically active (1S,9aS) N-[(9,9a-dihydro-3-oxo-1H,3H-oxazolo[3,4-a]indol-1-yl)methyl]acetamide (X, diastereomer B, [SS,RR-trans], prepared by the process of EXAMPLES 1, 3–7, 20 and 8–11) and (2) using the reagent listed below for each EXAMPLE (instead of phenylboronic acid) the title compound of the respective EXAMPLE is obtained.

REAGENTS 26 4-pyridyltrimethyltin
27 3-pyridyltrimethyltin
28 2-pyridyltrimethyltin
29 3-(6-cyano)pyridyltrimethyltin
30 2-(5-cyano)pyridyltrimethyltin
31 3-(6-aminomethyl)pyridylboronic acid
32 2-(5-aminomethyl)pyridylboronic acid
33 4-cyanophenylboronic acid
34 3-cyanophenylboronic acid

TITLE COMPOUNDS (1S, 9aS) N-[7-(4-Pyridyl)-9,9a-dihydro-3-oxo-1H,3H-oxazolo[3,4-a]indol-1-yl)methyl]acetamide (XI, diastereomer B, [SS-trans])
(1S, 9aS) N-[7-(3-Pyridyl)-9,9a-dihydro-3-oxo-1H,3H-oxazolo[3,4-a]indol-1-yl)methyl]acetamide (XI, diastereomer B, [SS-trans])
(1S, 9aS) N-[7-(2-Pyridyl)-9,9a-dihydro-3-oxo-1H,3H-oxazolo[3,4-a]indol-1-yl)methyl]acetamide (XI, diastereomer B, [SS-trans])
(1S, 9aS) N-[7-[3-(6-Cyano)pyridyl]-9,9a-dihydro-3-oxo-1H,3H-oxazolo[3,4-a]indol-1-yl)methyl]acetamide (XI, diastereomer B, [SS-trans])
(1S, 9aS) N-[7-[2-(5-Cyano)pyridyl)]-9,9a-dihydro-3-oxo-1H,3H-oxazolo[3,4-a]indol-1-yl)methyl]acetamide (XI, diastereometer B, [SS-trans])
(1S, 9aS) N-[7-[3-(6-Aminomethyl)pyridyl]-9,9a-dihydro-3-oxo-1H,3H-oxozolo[3,4-a]indol-1-yl)methyl]acetamide (XI, diastereomer B, [SS-trans])
(1S, 9aS) N-[7-[3-(5-Aminomethyl)pyridyl]-9,9a-dihydro-3-oxo-1H,3H-oxazolo[3,4-a]indol-1-yl)methyl]acetamide (XI, diastereomer B, [SS-trans])
(1S, 9aS) N-[7-(4-Cyanophenyl)-9,9a-dihydro-3-oxo-1H,3H-oxazolo[3,4-a]indol-1-yl)methyl]acetamide (XI, diastereomer B, [SS-trans])
(1S, 9aS) N-[7-(3-Cyanophenyl)-9,9a-dihydro-3-oxo-1H,3H-oxazolo[3,4-a]indol-1-yl)methyl]acetamide (XI, diastereomer B, [SS-trans])

EXAMPLE 35

(1S, 9aS) N-[7-(4-Pyridyl-N-oxide)-9,9a-dihydro-3-oxo-1H,3H-oxazolo[3,4-a]indol-1-yl)methyl]acetamide (XI, diastereomer B, [SS-trans])

(1S, 9aS) N-[7-(4-Pyridyl)-9,9a-dihydro-3-oxo-1H,3H-oxazolo[3,4-a]indol-1-yl)methyl]acetamide (XI, EXAMPLE 26, diastereomer B, [SS-trans]) is treated with excess m-chloroperbenzoic acid in methylene chloride at about 0° followed by the addition of dimethylsulfide. Aqueous workup and concentration gives the title compound.

EXAMPLE 36

(1S, 9aS) N-[7-(4-Methylsulphonylphenyl)-9,9a-dihydro-3-oxo-1H,3H-oxazolo[3,4-a]indol-1-yl)methyl]acetamide (XI, diastereomer B, [SS-trans])

Following the general procedure of EXAMPLE 25 and starting with (1S, 9aS) N-[(7-bromo-9,9a-dihydro-3-oxo-1H,3H-oxazolo[3,4-a]indol-1-yl)-methyl]acetamide, but using 4-methylmercaptophenylboronic acid, 7-[4-methylthiophenyl)phenyl]-9,9a-dihydro-3-oxo-1H,3H-oxazolo[3,4-a]indol-1-yl)methyl]acetamide is obtained. It is treated with excess m-chloroperbenzoic acid to give the title compound.

EXAMPLE 37

(1S, 9aS) N-[7-(4-Hydroxyethylphenyl)-9,9a-dihydro-3-oxo-1H,3H-oxazolo[3,4-a]indol-1-yl)methyl]acetamide (XI, diastereomer B, [SS-trans])

(1S,9aS) N-[(7-Acetyl-9,9a-dihydro-3-oxo-1H,3H-oxazolo[3,4-a]indol-1-yl)methyl]-acetamide (XI, EXAMPLE 22, diastereomer B, [SS-trans]) is treated with sodium borohydride in ethanol at about 20°, poured into water and extracted with ethyl acetate. The phases are separated and the organic phase is dried and concentrated under reduced pressure to give the title compound.

EXAMPLES 38–45

OPTICALLY PURE TRICYCLIC-FUSED 6[6,6,5] MEMBER RING OXAZOLIDINONES (XIX)

Following the general procedure of EXAMPLES 24 and 25 and making non-critical variations and (1) starting with optical active (1S,10aS/1S,10aR) [(4,9,10,10a-tetrahydro-3-oxo-1H,3H-oxazolo[3,4-a]quinol-1-yl)methyl]acetamide (XIX, EXAMPLE 23A, diastereomers B/A, [SS,RR-trans/SR,RS-cis]) and (2) using the reagent listed below for each EXAMPLE the title compound of the respective EXAMPLE is obtained.

REAGENTS 38 phenylboronic acid
39 4-pyridyltrimethyltin
40 3-pyridyltrimethyltin
41 2-pyridyltrimethyltin
42 phenylboronic acid
43 4-pyridyltrimethyltin
44 3-pyridyltrimethyltin
45 2-pyridyltrimethyltin

TITLE COMPOUNDS (1S, 10aS) [7-Phenyl-4,4a,9,10-tetrahydro-3-oxo-1H,3H-oxazolo[3,4-a]quinol-1-yl)methyl]acetamide (XIX, [SS-trans])

(1S, 10aS) [7-(4-Pyridyl)-4,4a,9, 10-tetrahydro-3-oxo-1H,3H-oxazolo[3,4-a]quinol-1-yl)methyl]acetamide (XIX, [SS-trans])

(1S, 10aS) [7-(3-Pyridyl)-4,4a,9,10-tetrahydro-3-oxo-1H,3H-oxazolo[3,4-a]quinol-1-yl)methyl]acetamide (XIX, [SS-trans])

(1S, 10aS) [7-(2-Pyridyl)-4,4a,9,10-tetrahydro-3-oxo-1H,3H-oxazolo[3,4-a]quinol-1-yl)methyl]acetamide (XIX, [SS-trans])

(1S, 10aR) [7-Phenyl-4,4a,9,10-tetrahydro-3-oxo-1H,3H-oxazolo[3,4-a]quinol-1-yl)methyl]acetamide (XIX, [SR-cis])

(1S, 10aR) [7-(4-Pyridyl)-4,4a,9,10-tetrahydro-3-oxo-1H,3H-oxazolo[3,4-a]quinol-1-yl)methyl]acetamide (XIX, [SR-cis])

(1S, 10aR) [7-(3-Pyridyl)-4,4a,9,10-tetrahydro-3-oxo-1H,3H-oxazolo[3,4-a]quinol-1-yl)methyl]acetamide (XIX, [SR-cis])

(1S, 10aR) [7-(2-Pyridyl)-4,4a,9,10-tetrahydro-3-oxo-1H,3H-oxazolo[3,4-a]quinol-1-yl)methyl]acetamide (XIX, [SR-cis])

EXAMPLE 46

(+/−)-(1S,9aS),(1R,9aR)
N-[(7-Chloroacetyl-9,9a-dihydro-3-oxo-1H,3H-oxazolo[3,4-a]indol-1-yl)methyl]acetamide (XI, [SS,RR-trans])

Aluminum trichloride (1.076 g) is suspended in freshly distilled (over calcium hydride) methylene chloride (0.8 ml). The mixture is then cooled in an ice water bath and chloroacetyl chloride (220 μl) is added dropwise. After 10 minutes, (±) (1S,9aS/1R,9aR) N-[(9,9a-dihydro-3-oxo-1H,3H-oxazolo[3,4-a]indol-1-yl)methyl]acetamide (X, EXAMPLE 11, diastereomer B, [SS,RR-trans], 450 mg) is added as a solution in distilled methylene chloride (1.2 ml). The mixture is stirred in the ice water bath for 20 minutes then at 20°-25° for 1 hour. After this time the mixture is placed in a 50° oil bath for 1 hour. At the end of this time the reaction is determined to be complete by proton NMR of an aliquot of the reaction mixture. Upon cooling the mixture separates into two layers a dark tar on the bottom and a clear solvent layer on top. The solvent layer is removed and a small amount of ice and 2 ml of 1N hydrochloric acid is added to the tar. Upon stirring this mixture it became very violent and formed a solid. This solid is collected by vacuum filtration and dried in a vacuum oven to provide crude title compound. This crude material is adsorbed onto 40-63 μ silica and then placed on top of a 5 cm×2.5 cm 40-63 μ silica column and eluted with ethylacetate (800 ml). The appropriate fractions are pooled and concentrated to give the title compound which is recrystallized from methanol/methylene chloride (1/1) by evaporation of the solvent under nitrogen, mp=172°-174°; NMR (DMSO-d$_6$, 300 MHz) 8.31, 7.91, 7.34, 5.13, 4.76, 4.55, 3.53, 3.22 and 1.87 δ.

EXAMPLE 47

(+/−)-(1S,9aS),(1R,9aR)
N-[(7-Azidoacetyl-9,9a-dihydro-3-oxo-1H,3H-oxazol[3,4-a]indol-1-yl)methyl]acetamide (XI, [SS,RR-trans])

A mixture of (+/−)-(1S,9aS),(1R,9aR) N-[(7-chloroacetyl-9,9a-dihydro-3-oxo-1H,3H-oxazolo [3,4-a]indol-1-yl)methyl]acetamide (EXAMPLE 46, 43 mg) and sodium azide (82 mg) are stirred in aqueous tetrahydrofuran (66%) for 3 days. Acetone (1 ml) is added and the mixture was heated in an oil bath (38°-50°) for 8 hours then concentrated to an aqueous layer and extracted with ethylacetate (6×2 ml). The combined organic layers are dried over magnesium sulfate and concentrated to provide the product as as an oil. The oil is taken up in methylene chloride/methanol and then placed on a 1000 μsilica preprative plate and developed in methanol/ethylacetate (10/90, 2×) to give the title compound as an oil, NMR (CDCl$_3$, 300 MHz) 7.79, 7.43, 6.45, 4.63, 4.53, 3.75, 3.38, 3.14 and 2.08 δ; IR (CHCl$_3$) 2100, 1760, 1670 and 1360 cm$^{-1}$.

EXAMPLE 48

(1S,9aS)
N-[(7-Chloroacetyl-9,9a-dihydro-3-oxo-1H,3H-oxazolo[3,4-a]indol-1-yl)methyl]acetamide (XI)

Aluminum trichloride (1.076 g) is suspended in freshly distilled (over calcium hydride) methylene chloride (0.8 ml). The mixture is then cooled in an ice water bath and chloroacetyl chloride (220 μl) is added dropwise. After 10 minutes, (1S,9aS) N-[(9,9a-dihydro-3-oxo-1H,3H-oxazolo[3,4-a]indol-1-yl)methyl]acetamide (X, EXAMPLE 21, diastereomer B, [SS-trans], 450 mg) is added as a solution in distilled methylene chloride (1.2 ml). The mixture is stirred in the ice water bath for 20 minutes then at 20°-25° for 1 hour. After this time the mixture is placed in a 50° oil bath for 1 hour. At the end of this time the reaction is determined to be complete by proton NMR of an aliquot of the reaction mixture. Upon cooling the mixture separates into two layers a dark tar on the bottom and a clear solvent layer on top. The solvent layer is removed and a small amount of ice and 2 ml of 1N hydrochloric acid is added to the tar. Upon stirring this mixture it became very violent and formed a solid. This solid is collected by vacuum filtration and dried in a vacuum oven to provide crude title compound. This crude material is adsorbed onto 40-63 μsilica and then placed on top of a 5 cm×2.5 cm 40-63 μsilica column and eluted with ethylacetate (800 ml). The appropriate fractions are pooled and concentrated to give the title compound which is recrystallized from methanol/methylene chloride (1/1) by evaporation of the solvent under nitrogen.

EXAMPLE 49

(1S,9aS)
N-[(7-Azidoacetyl-9,9a-dihydro-3-oxo-1H,3H-oxazolo [3,4-a]indol-1-yl)methyl]acetamide (XI)

A mixture of (1S,9aS) N-[(7-chloroacetyl-9,9a-dihydro-3-oxo-1H,3H-oxazolo[3,4-a]indol-1-yl)methyl]acetamide (EXAMPLE 48, 43 mg) and sodium azide (82 mg) are stirred in aqueous tetrahydrofuran (66%) for 3 days. Acetone (1 ml) is added and the mixture was heated in an oil bath (38°-50°) for 8 hours then concentrated to an aqueous layer and extracted with ethylacetate (6×2 ml). The combined organic layers are dried over magnesium sulfate and concentrated to provide the product as as an oil. The oil is taken up in methylene chloride/methanol and then placed on a 100 μsilica preprative plate and developed in methanol/ethylacetate (10/90, 2×) to give the title compound.

CHART A
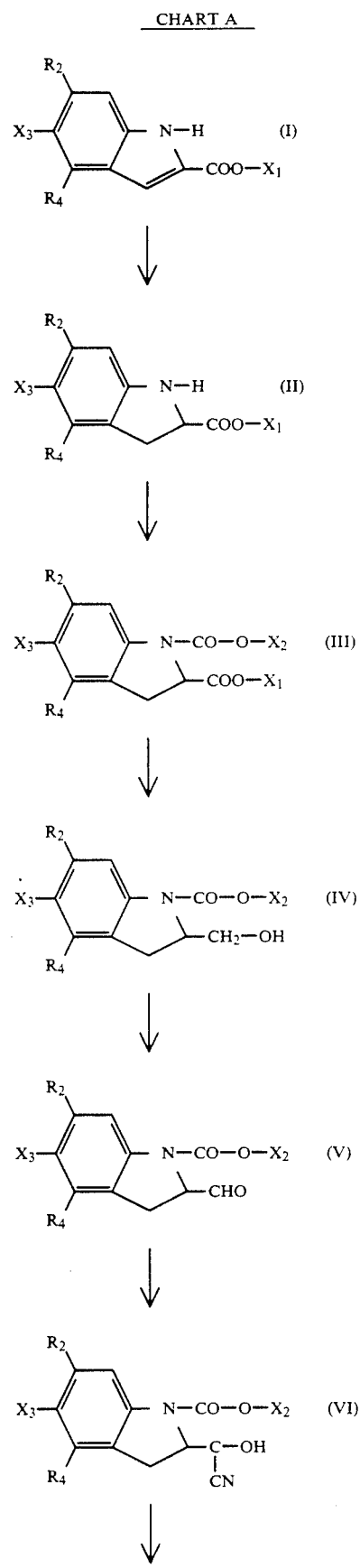
-continued
CHART A
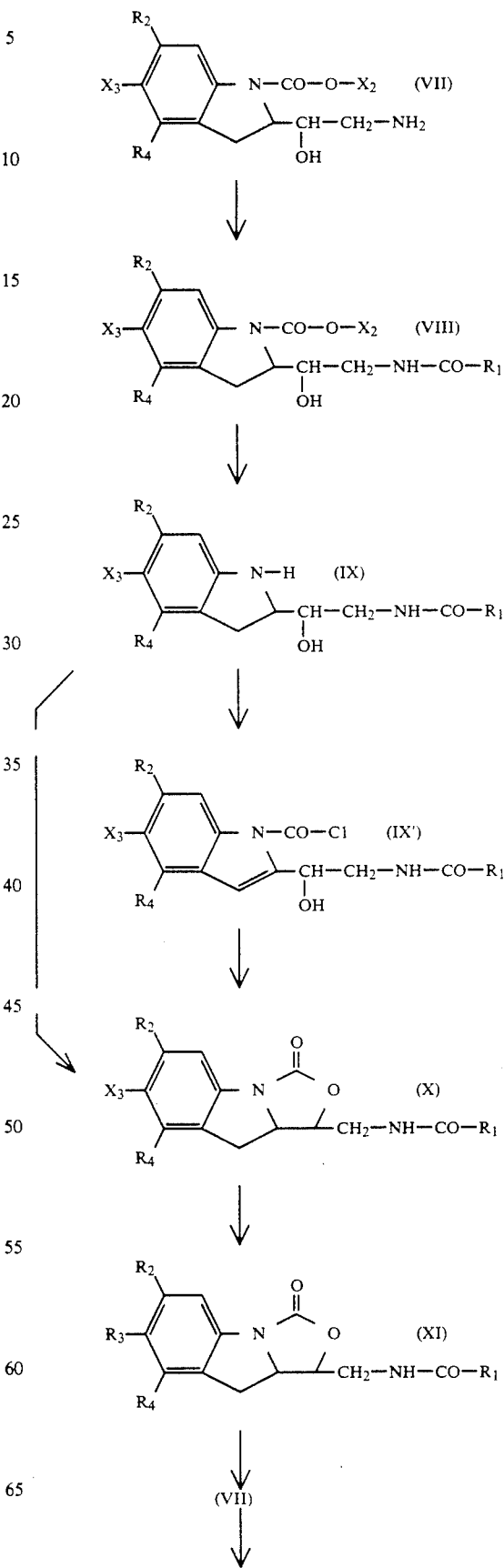

-continued
CHART A
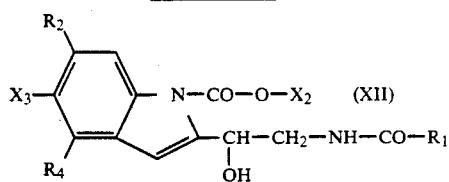
(XII)
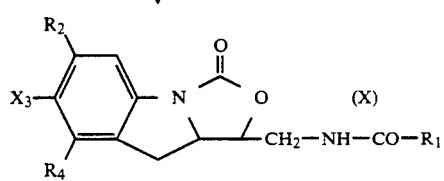
(X)
(VIII)
CHART B
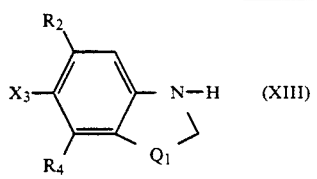
(XIII)
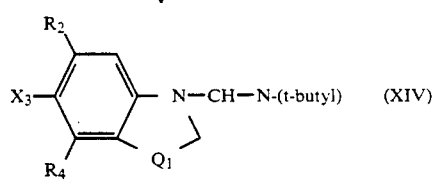
(XIV)
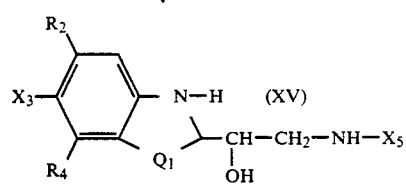
(XV)
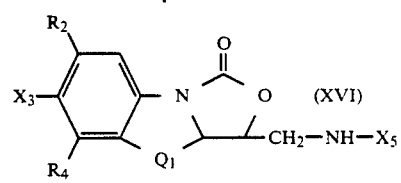
(XVI)
-continued
CHART B
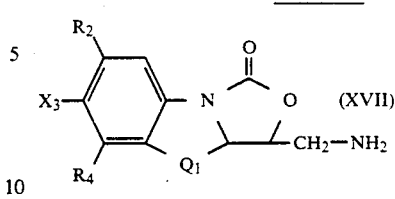
(XVII)
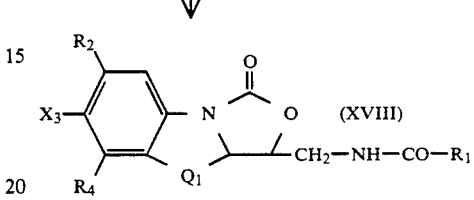
(XVIII)
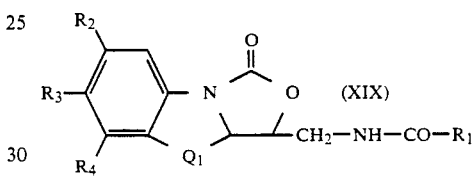
(XIX)
CHART C
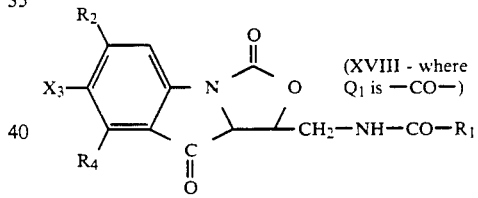
(XVIII - where $Q_1$ is $-CO-$)
$R_{7-1}MgX$
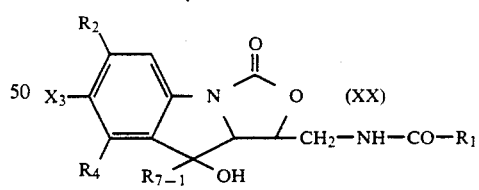
(XX)
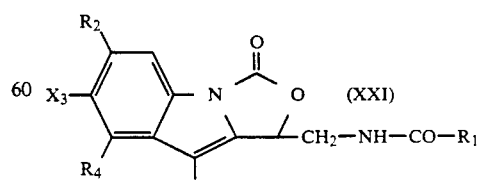
(XXI)
(XVIII-where $Q_1$ is $-CO-$)

-continued
CHART C
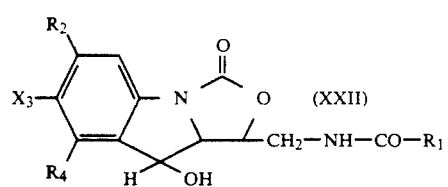
(XXII)
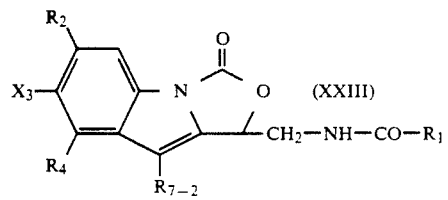
(XXIII)
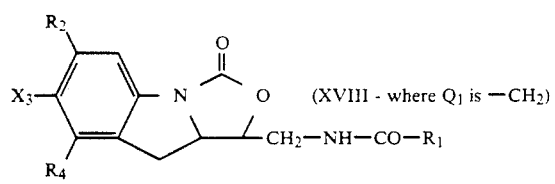
(XVIII - where Q₁ is —CH₂)
CHART D
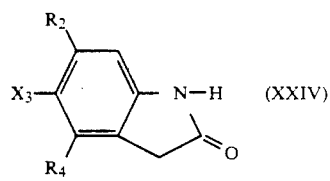
(XXIV)
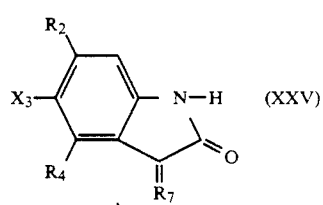
(XXV)
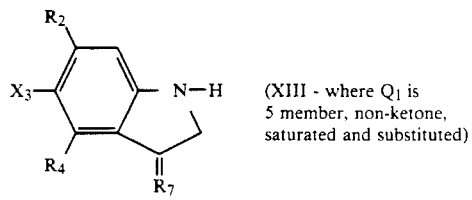
(XIII - where Q₁ is 5 member, non-ketone, saturated and substituted)
CHART E
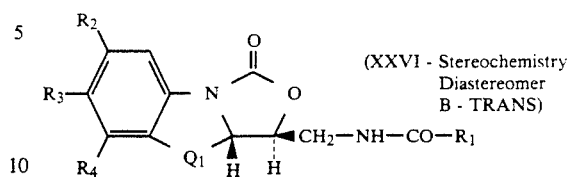
(XXVI - Stereochemistry Diastereomer B - TRANS)
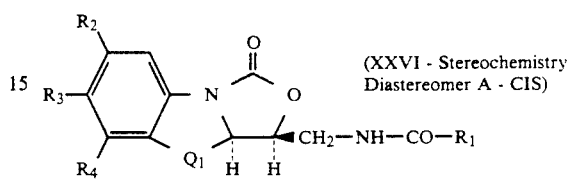
(XXVI - Stereochemistry Diastereomer A - CIS)
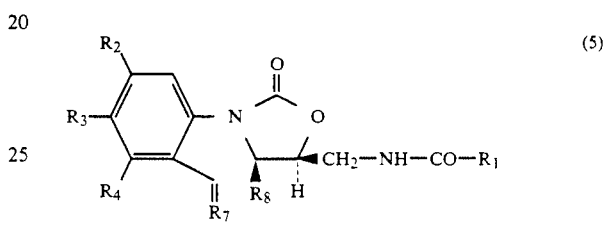
(5)
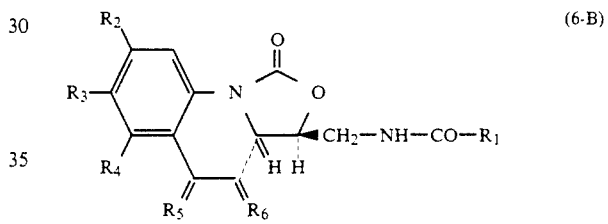
(6-B)
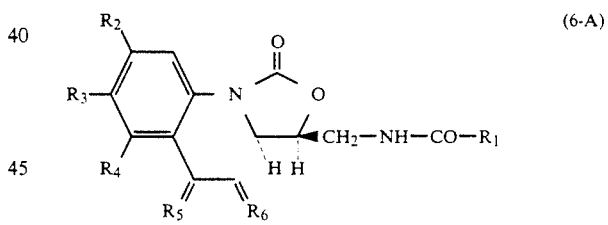
(6-A)
CHART F
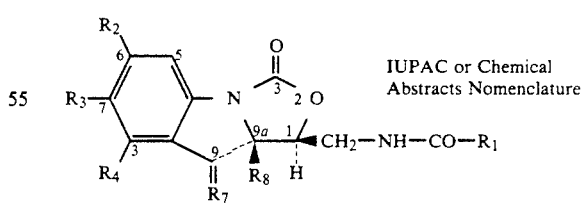
IUPAC or Chemical Abstracts Nomenclature
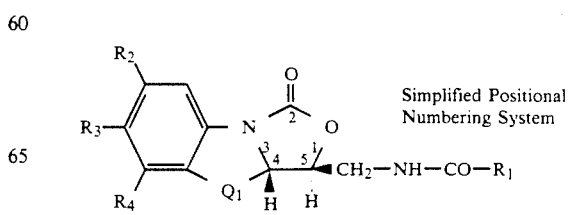
Simplified Positional Numbering System -continued
CHART F

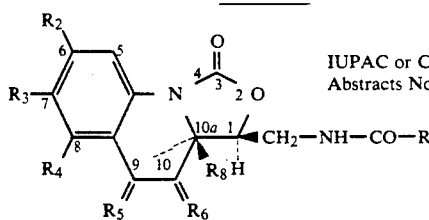

IUPAC or Chemical Abstracts Nomenclature

I claim:
1. A tricyclic-fused 6-member [6,6,5] ring oxazolidinones of formula (6-B)

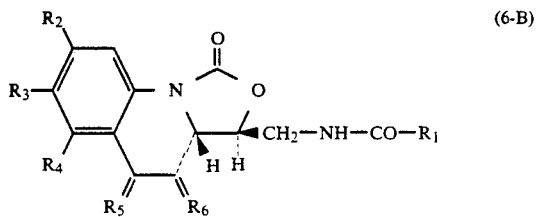

where
(I) $R_1$ is —H,
$C_1$-$C_{12}$ alkyl optionally substituted with 1-3 Cl,
$C_3$-$C_{12}$ cycloalkyl,
$C_5$-$C_{12}$ alkenyl containing one double bond,
—$\phi$ optionally substituted with 1-3 —OH, —OCH$_3$, —OC$_2$H$_5$, —NO$_2$, —F, —Cl, —Br, —COOH and —SO$_3$H, —N($R_{1-1}$)($R_{1-2}$) where $R_{1-1}$ and $R_{1-2}$ are the same or different and are —H, $C_1$-$C_2$ alkyl, furanyl,
tetrahydrofuranyl,
2-thiophene,
pyrrolidinyl,
pyridinyl,
—O—$R_{1-3}$ where $R_{1-3}$ is $C_1$-$C_4$ alkyl,
—NH$_2$,
—NHR$_{1-4}$ where $R_{1-4}$ is $C_1$-$C_3$ alkyl or —$\phi$,
—NR$_{1-4}$R$_{1-5}$ where $R_{1-5}$ is $C_1$-$C_3$ alkyl and $R_{1-4}$ is as defined above and where $R_{1-4}$ and $R_{1-5}$ can be taken together with the attached nitrogen atom to form morpholin 4-yl
—CH$_2$—OH,
—CH$_2$—OR$_{1-6}$ where $R_{1-6}$ is $C_1$-$C_4$ alkyl or —CO—$R_{1-7}$ where $R_{1-7}$ is $C_1$-$C_4$ alkyl or —$\phi$;
(II) $R_2$ and $R_4$ are the same or different and are
—H,
—OH,
—F, —Cl, —Br, —I,
—O—CO—$R_{2-1}$ where $R_{2-1}$ is $C_1$-$C_3$ alkyl or —$\phi$,
(III) $R_3$ is —H, —F, —Cl, —Br, —I, —O—CH$_3$, —O—C$_2$H$_5$, —CO—$R_{3-1}$ where $R_{3-1}$ is $C_1$-$C_4$ alkyl optionally substituted with 1 or 2 —F or —Cl, or 1 —OH,
—CO—CH$_2$—O—CH$_2$—$\phi$,
—CO—CH$_2$—O—$R_{3-2}$ where $R_{3-2}$ is $C_1$-$C_2$ alkyl or —$\phi$,
—CO—CH$_2$—N$_3$,
—CO—CH$_2$—NH—CO—$R_{3-3}$ where $R_{3-3}$ is $C_1$-$C_2$ alkyl or —$\phi$,
—C(CH$_3$)=N—OH,
—C(CH$_3$)=N—O—$R_{3-4}$ where $R_{3-4}$ is $C_1$-$C_2$ alkyl
—CO—CH$_2$—NR$_{3-5}$R$_{3-6}$ where $R_{3-5}$ is —H, —CH$_3$, —C$_2$H$_5$ or —$\phi$ and where $R_{3-6}$ is —H, —CH$_3$ or —C$_2$H$_5$,
—SO$_2$—CH$_3$,
—SO$_2$—$\phi$,
—SO—CH$_3$,
—SO—$\phi$,
—SO$_2$—NH$_2$,
—S—$R_{3-7}$ where $R_{3-7}$ is —H, —CH$_3$, —C$_2$H$_5$ or —$\phi$,
—CO—CH$_2$—O—CO—$R_{3-8}$ where $R_{3-8}$ is $C_1$-$C_6$ alkyl or —$\phi$,
—$\phi$ optionally substituted —CN,
—C≡CH, —C≡C—CH$_3$, —C≡C—CH$_2$—OH,
—N$_3$, —NO$_2$,
—O—,
—COOH, —SO$_2$—OH,
—F, —Cl, —Br, —I, —OH,
—NH$_2$, —N($R_{3-9}$)($R_{3-10}$) where $R_{3-9}$ and $R_{3-10}$ are the same or different and are selected from the group consisting of —H, $C_1$-$C_3$ alkyl or —$\phi$, 1-pyrrolidyl,
—CO—[$C_1$-$C_4$ alkyl], —CO—CH$_2$—N$_3$,
—CHOH—[$C_1$-$C_4$ alkyl], —CH$_2$—OH,
—CH$_2$—NH$_2$, —CH$_2$—N($R_{3-9}$)($R_{3-10}$) where $R_{3-9}$ and $R_{3-10}$ are as defined above,
—CH$_2$—N$_3$,
—CH$_2$—NH—CO—$R_{3-9}$ where $R_{3-9}$ is as defined above,
—S—[$C_1$-$C_4$ alkyl], —SO—[$C_1$-$C_4$ alkyl], —SO$_2$—[$C_1$-$C_4$ alkyl],
—(CH$_3$)=N—OH, —(CH$_3$)=N—O—[$C_1$-$C_4$ alkyl],
—NH—COO—[$C_1$-$C_4$ alkyl], —NH—SO$_2$—[$C_1$-$C_4$ alkyl],
—NH—CO—[$C_1$-$C_4$ alkyl], —NH—CO—$\phi$,
—S—CN,
—$\phi$ optionally substituted with 1 or 2 —F, —Cl, —OH,
—CO—N($R_{3-9}$)($R_{3-10}$) where $R_{3-9}$ and $R_{3-10}$ are as defined above,
$C_1$-$C_{12}$ alkyl, $C_2$-$C_{12}$ alkenyl containing 1, 2 or 3 double bonds, with the proviso that at least one of $R_2$, $R_3$ and $R_4$ is -H, and either
(IVA) $R_5$ is $R_{5-1}$:$R_{5-2}$ and $R_6$ is $R_{6-1}$:$R_{6-2}$ where one of $R_{5-1}$ or $R_{5-2}$ is taken with one of $R_{6-1}$ or $R_{6-2}$ to form a second bond between the carbon atoms to which they are attached and the other of $R_{5-1}$ or $R_{5-2}$ and $R_{6-1}$ or $R_{6-2}$ is -H, or
(IVB) $R_5$ is $R_{5-3}$:$R_{5-4}$ where one of $R_{5-3}$ and $R_{5-4}$ is -H and the other of $R_{5-3}$ and $R_{5-4}$ is -H, —OH or —O—CO—$R_{5-5}$ where $R_{5-5}$ is $C_1$-$C_3$ alkyl or —$\phi$ optionally substituted with 1 or 2 —F, —Cl, —OH, or —OCH$_3$,
(IVC) $R_6$ is $R_{6-3}$:$R_{6-4}$ where one of $R_{6-3}$ and $R_{6-4}$ is -H and the other of $R_{6-3}$ and $R_{6-4}$ is -H, —OH or —O—CO—$R_{6-5}$ where $R_{6-5}$ is $C_1$-$C_3$ alkyl or —$\phi$ optionally substituted with 1 or 2 —F, —Cl, —OH, or —OCH$_3$, and pharmaceutically acceptable salts thereof.
2. A tricyclic-fused 6-member [6,6,5] ring oxazolidinone (6) according to claim 1 where $R_1$ is selected from the group consisting of —H, $C_1$-$C_6$ alkyl, $C_3$-$C_6$ cycloalkyl, —OCH$_3$ and —CHCl$_2$.
3. A tricyclic-fused 6-member [6,6,5] ring oxazolidinone (6) according to claim 1 where $R_2$ is —H.
4. A tricyclic-fused 6-member [6,6,5] ring oxazolidinone (6) according to claim 1 where $R_4$ is —H.
5. A tricyclic-fused 6-member [6,6,5] ring oxazolidinone (6) according to claim 1 where $R_3$ is —H, —CO—CH$_3$, —CO—CH$_2$—Cl, —CO—CH$_2$—OH, —CO—CHF$_2$ and —CO—CH$_2$—N$_3$.

6. A tricyclic-fused 6-member [6,6,5] ring oxazolidinone (6) according to claim 1 where R$_5$ is R$_{5-3}$:R$_{5-4}$ where both of R$_{5-3}$ and R$_{5-4}$ are —H.

7. A tricyclic-fused 6-member [6,6,5] ring oxazolidinone (6) according to claim 1 where R$_6$ is R$_{6-3}$:R$_{6-4}$ where both of R$_{6-3}$ and R$_{6-4}$ are —H.

8. A tricyclic-fused 6-member [6,6,5] ring oxazolidinone (6) according to claim 1 which is
(1S,10aS) [(7-acetyl-4,4a,9,10-tetrahydro-3-oxo-1H,3H-oxazolo[3,4-a]quinol-1-yl)methyl]acetamide,
(1S,10aS) [(4,9,10,10a-tetrahydro-3-oxo-1H,3H-oxazolo[3,4-a]quinol-1-yl)methyl]acetamide,
(1S, 10aS) [7-phenyl-4,4a,9,10-tetrahydro-3-oxo-1H,3H-oxazolo[3,4-a]quinol-1-yl)methyl]acetamide,

* * * * *